(12) United States Patent
Fukuda et al.

(10) Patent No.: US 7,361,182 B2
(45) Date of Patent: Apr. 22, 2008

(54) MEDICAL LANCET

(75) Inventors: Mitsuo Fukuda, Hyogo (JP); Seiji Aoyagi, Osaka (JP)

(73) Assignee: Lightnix, Inc., Hyogo (JP)

( * ) Notice: Subject to any disclaimer, the term of this patent is extended or adjusted under 35 U.S.C. 154(b) by 623 days.

(21) Appl. No.: 10/784,877

(22) Filed: Feb. 24, 2004

(65) Prior Publication Data

US 2005/0149088 A1    Jul. 7, 2005

(30) Foreign Application Priority Data

Dec. 19, 2003    (JP)    ............................ P2003-422999

(51) Int. Cl.
*A61B 17/32*    (2006.01)
(52) U.S. Cl. .................................... 606/181
(58) Field of Classification Search ................. 606/75, 606/222, 223, 23, 28, 41, 43–45, 167, 170, 606/181, 184–189; 600/583; 411/494, 496–498, 411/490, 492
See application file for complete search history.

(56) References Cited

U.S. PATENT DOCUMENTS

| 4,924,865 | A | * | 5/1990 | Bays et al. .................... 606/77 |
| 5,752,942 | A |   | 5/1998 | Doyle et al. |
| 2003/0028125 | A1 | | 2/2003 | Yuzhakov et al. |
| 2004/0131437 | A1 | | 7/2004 | Kasai et al. |

FOREIGN PATENT DOCUMENTS

| EP | 0 137 975 B1 | 4/1985 |
| JP | UM 53-68594 A | 6/1978 |
| JP | 61-31167 A | 2/1986 |
| JP | 2001-509399 | 7/2001 |
| JP | 2002-45423 A | 2/2002 |
| JP | 2003116962 | 4/2003 |
| JP | 2003-275327 | 9/2003 |
| WO | WO 99/00155 | 1/1999 |
| WO | WO 03/037403 A1 | 5/2003 |
| WO | WO 03/059431 A1 | 7/2003 |

OTHER PUBLICATIONS

Oka et al., "Fabrication of a Micro Needle for a Trace Blood Test," Mar. 7, 2001 (pp. 59-62).
Japanese Office Action (dated Jun. 19, 2007) for Japanese Patent Application 2006-199497 is provided for the purposes of certification under 37 C.F.R. §§1.97(e) and 1.704(d).

* cited by examiner

*Primary Examiner*—(Jackie) Tan-Uyen Ho
*Assistant Examiner*—Melanie Tyson
(74) *Attorney, Agent, or Firm*—Harness, Dickey & Pierce, P.L.C.

(57) ABSTRACT

One of aspects of the present invention is to provide a medical lancet, which includes a first ascending region, a descending region, and a second ascending region subsequently and integrally formed of biodegradable material. Those regions extend from a point of the lancet in a predetermined direction, and each of the regions having triangular cross sections taken along any planes perpendicular to the predetermined direction. The first and second ascending regions have the triangular cross sections of which area monotonically increases as being away from the point. Also, the descending region has the triangular cross sections of which area monotonically decreases as being away from the point. The first and second ascending regions have the largest cross section having substantially the same size and shape to each other.

26 Claims, 18 Drawing Sheets

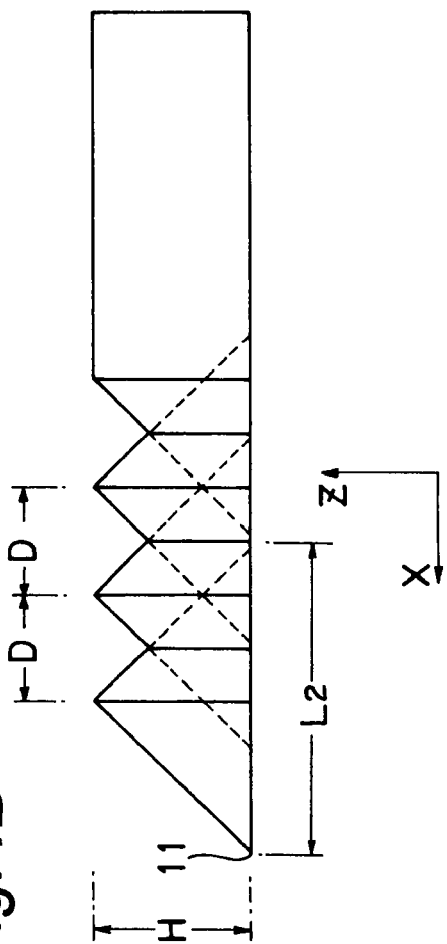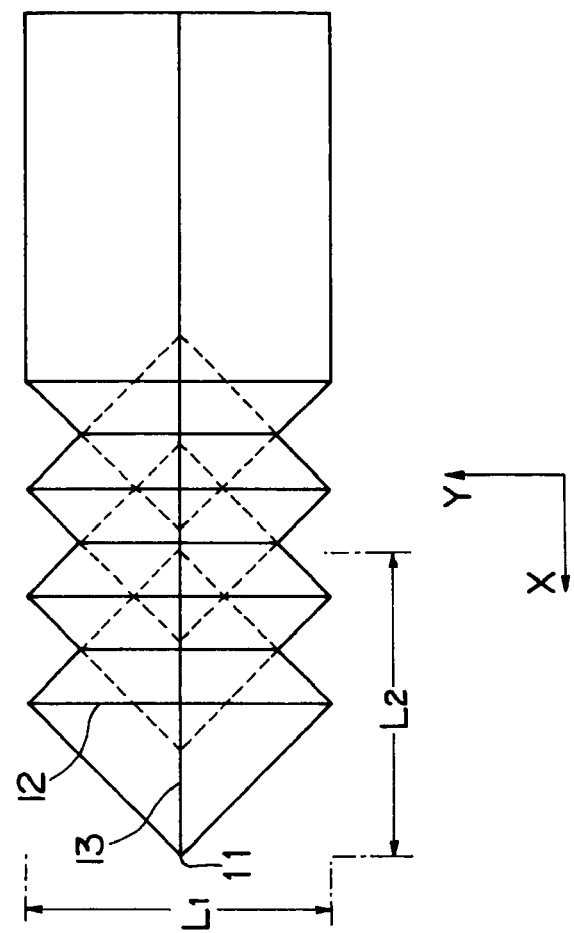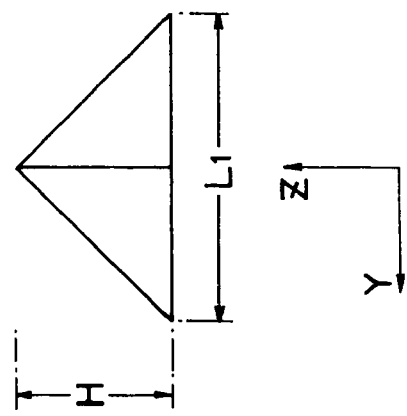

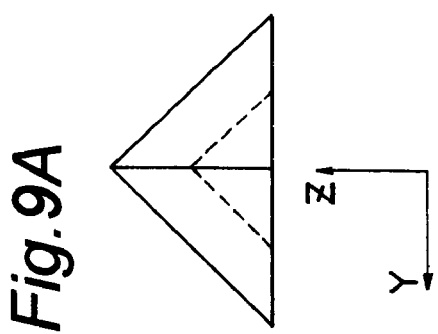
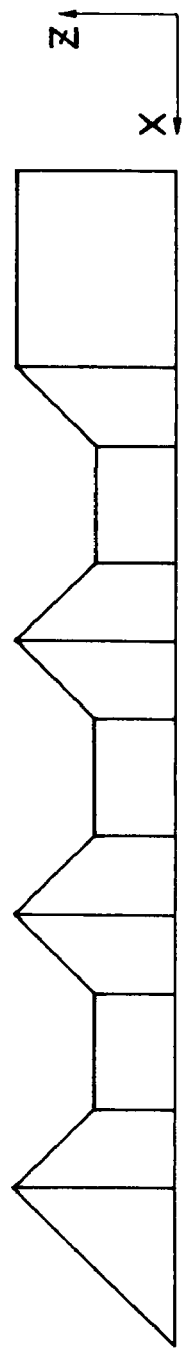
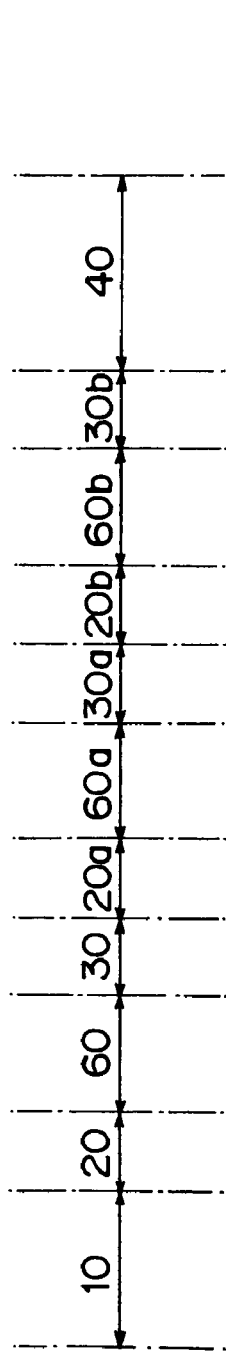
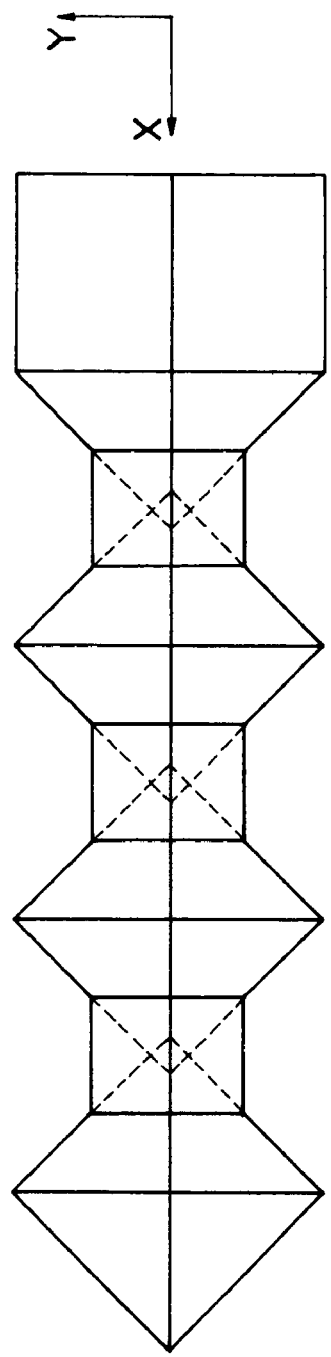

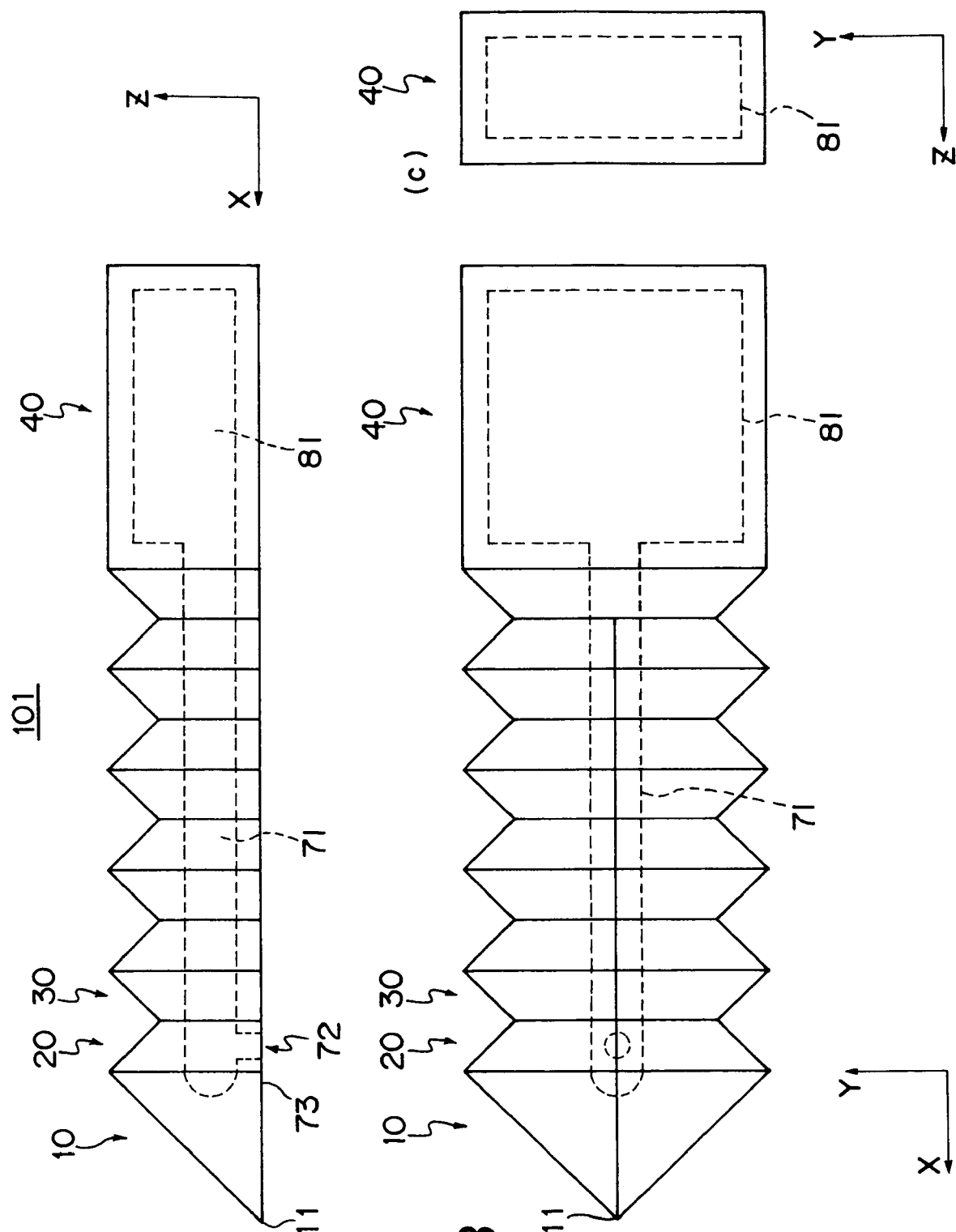

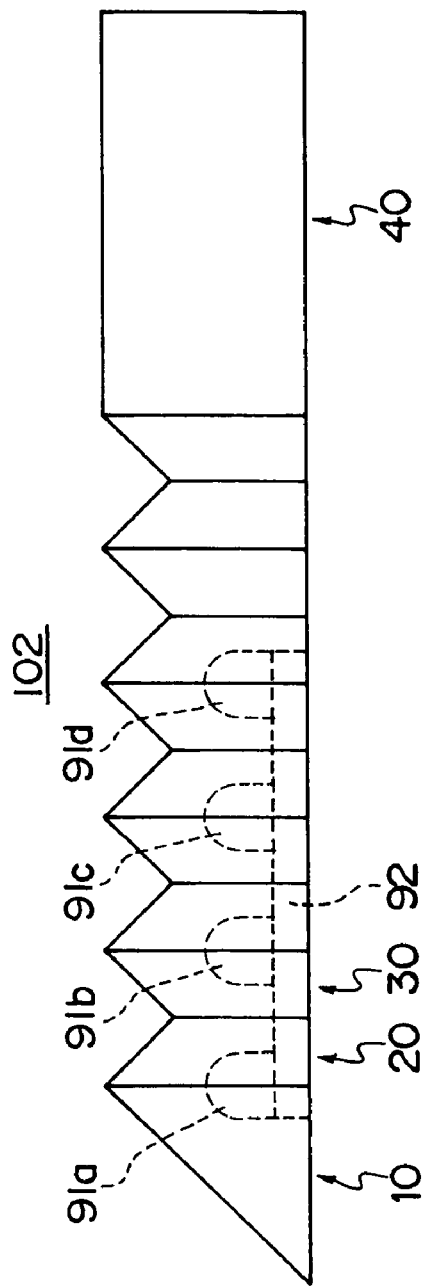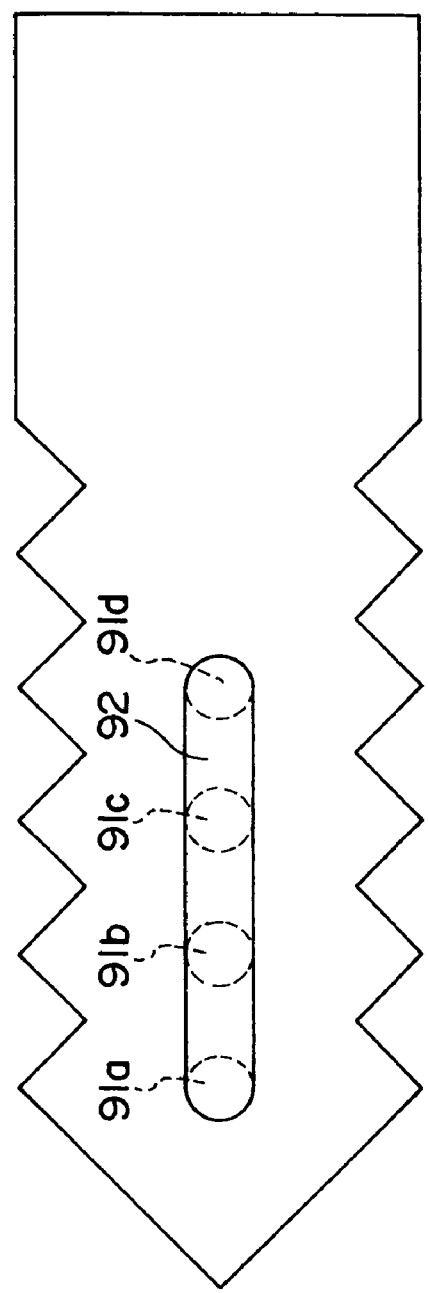
Fig.14A
Fig.14B

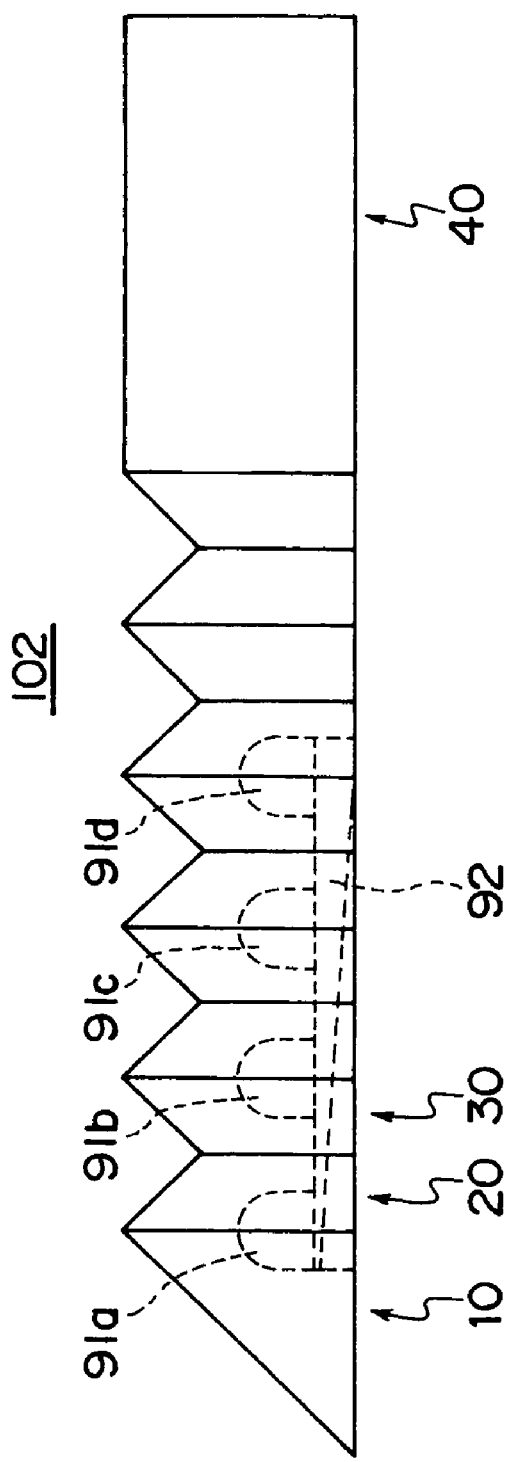
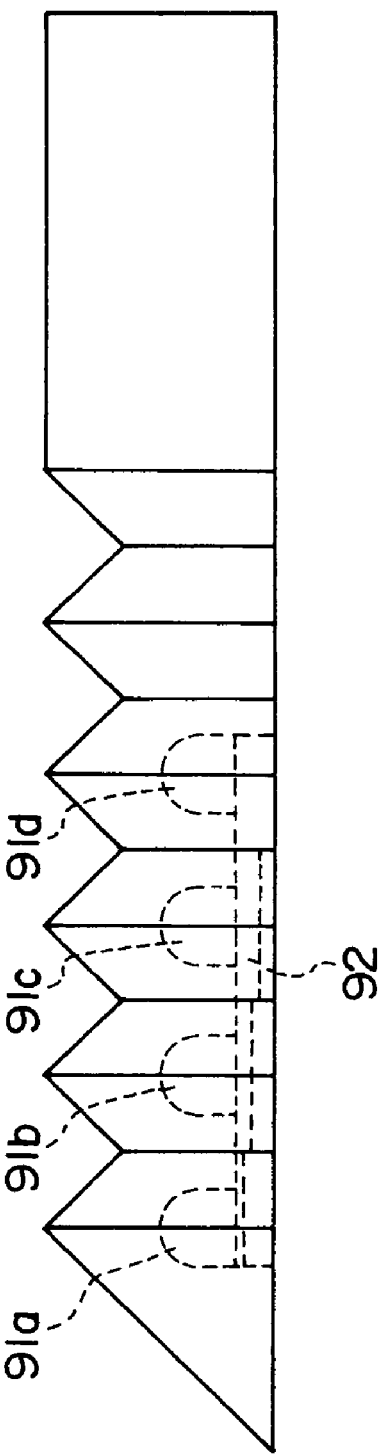
Fig. 15A
Fig. 15B

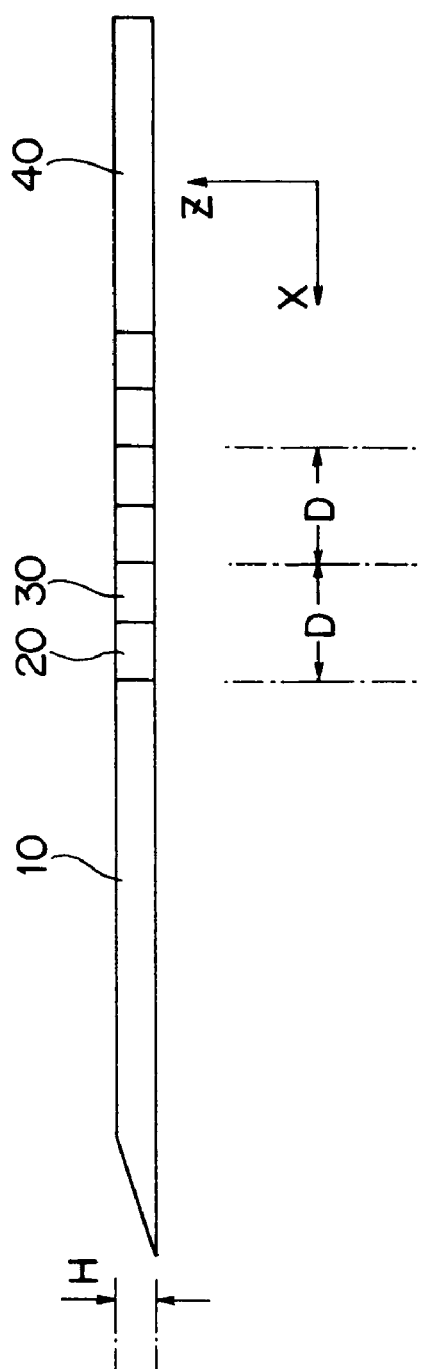
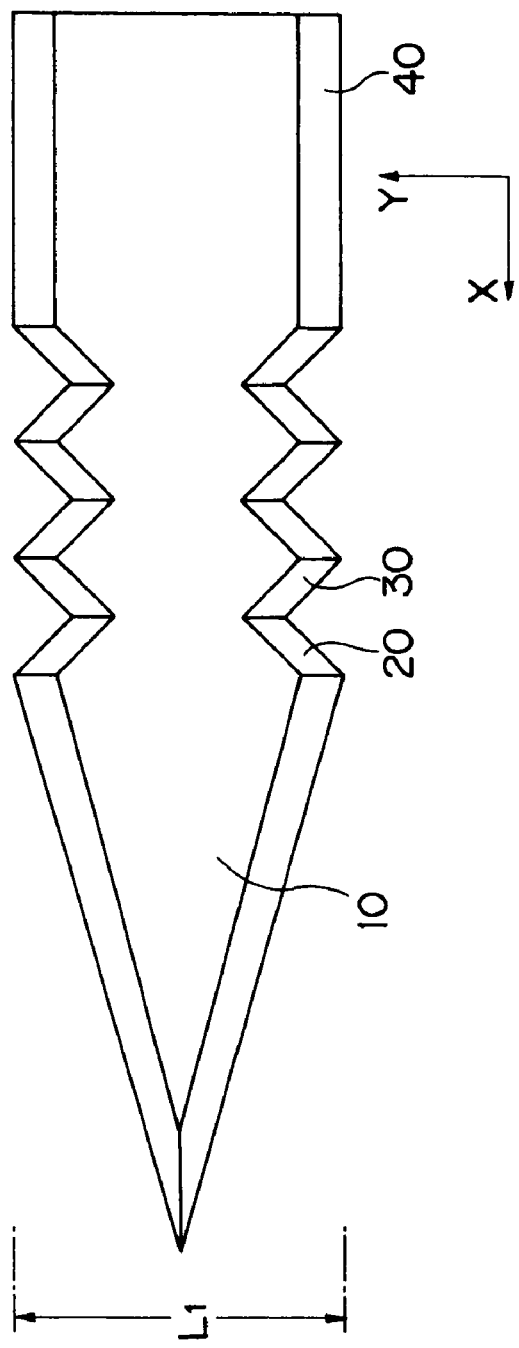
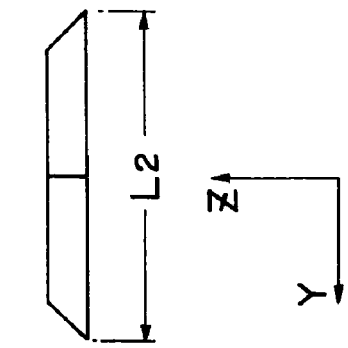
Fig.18A
Fig.18B
Fig.18C

MEDICAL LANCET

CROSS-REFERENCE TO RELATED APPLICATIONS

A related patent application is a commonly assigned Japanese Patent Application No. 2003-422999 filed on Dec. 19, 2003, which is incorporated herein by reference into the present patent application.

BACKGROUND OF THE INVENTION

1) Technical Field of the Invention

The present invention relates to a medical lancet, and in particular, to the medical lancet made of biodegradable material such as poly lactic acid.

2) Description of Related Arts

In general, when a patient has a hypodermic injection, a needle is shot at an appropriate portion of the body such as skin and muscle to inject medicine inside the patient. Also, a diabetic uses a lancet to sample a small amount of his or her blood by stinging it on any suitable portions, e.g., at fingertip, for routine measurement of the blood sugar. The patient having such a needle or lancet pierced into the body, especially children, sometimes suffers unendurable pain or uncomfortableness. Also, a substantial area of cells around the tingled portion may often be damaged, requiring some time to be cured. Therefore, there has been long-felt desire to develop a less invasive needle and lancet, minimizing the pain (unpleasantness) experienced by the patient.

In fact, some of injection needles have been proposed with a little pain to the patient. For example, the U.S. Pat. No. 5,752,942, corresponding to the Japanese Patent Publication Application JPA 10-57490, explains the primary reason of the patient's pain that the needle point "catches" the skin or flesh as the needle is penetrating. Also, it discloses a hypodermic needle with multi-beveled point geometry so as to reduce the pain.

The present inventors has found the reason of the pain more precisely as described below, and made the invention based upon the knowledge. As the needle is penetrating into the tissue such as skin and flesh of the patient, a contacting surface between an outer surface of the needle and the tissue of the patient is increased so that the frictional force therebetween becomes greater and the peripheral cells adjacent to the needle are drawn inside deeply. To this end, the peripheral cells are extremely deformed by the physical stress due to the frictional force, and may often be burst away (collapsed) so that a pain-producing chemical mediator such as histamine and bradykinin is released within the tissue, thereby hurting the patient. Also, the peripheral cells collapsed by the physical stress extend across the substantial region, which makes more painful and less healable. As described above, the conventional needle is highly invasive to pierce the tissue of the patient.

Also, the medical lancet is used to sampling a drop of blood by stinging into the tissue at the appropriate portion of the patient's body. Thus, while there are possible drawbacks as the above-mentioned needles, it is highly desired to provide the medical lancet designed less invasive by minimizing the frictional stress to the peripheral tissue of the patient. According to the medical lancet of the present invention, it cuts the peripheral cells as few as possible and wedges away the intact tissues into the deep inside, as will be described herein in detail.

Therefore, one of the aspects of the present invention is to provide a less invasive medical lancet giving less pain to the patient.

Meanwhile, such a needle and lancet are disposed immediately after once used, to prevent various infections. Since the conventional needle and lancet are generally made of metal, they are usually treated as industrial waste for landfill rather than as the burnable waste. However, it now raises a serious social problem because of the huge amount of the industrial waste and the risk of the infections thereby.

Therefore, another one of the aspects of the present invention is to provide the medical lancet integrally formed of biodegradable material such as Poly Lactic Acid, which can be degraded by micro-organisms once deposited in the soil.

SUMMARY OF THE INVENTION

According to the first aspect of the present invention, a medical lancet includes a first ascending region, a descending region, and a second ascending region subsequently and integrally formed of biodegradable material. Those regions extend from a point of the lancet in a predetermined direction, and each of the regions having triangular cross sections taken along any planes perpendicular to the predetermined direction. The first and second ascending regions have the triangular cross sections of which area monotonically increases as being away from the point. Also, the descending region has the triangular cross sections of which area monotonically decreases as being away from the point. The first and second ascending regions have the largest cross section having substantially the same size and shape to each other.

Preferably, the medical lancet further includes at least one additional descending and ascending regions subsequently and integrally formed of biodegradable material and connected to the second ascending region, extending in the predetermined direction. Each of the additional descending and ascending regions has the triangular cross sections taken along any planes perpendicular to the predetermined direction, of which area monotonically increases and decreases as being away from the point, respectively. Also, the first and second ascending regions have the largest cross section having substantially the same size and shape to each other.

Also preferably, the smallest cross, section in the descending region is similar to the largest cross section in the ascending regions, and the smallest cross section in the descending region has the area greater than one-fourth of the area of the largest cross section in the ascending regions.

More preferably, the smallest cross section in the descending region has the area greater than four-ninths of the area of the largest cross section in the ascending regions.

Further, the largest cross sections in the first and second ascending regions are spaced away from each other by a gap greater than one micron.

Also preferably, a continuous curved portion is provided between the descending region and the second ascending region for smoothly connecting thereof.

Alternatively, the lancet further includes a constant region integrally formed of biodegradable material between the descending region and the second ascending region, having triangular cross sections taken along any planes perpendicular to the predetermined direction, of which area is constant.

Preferably, the area of the triangular cross sections in the first and second ascending regions are linearly increased at first and second increasing rates, respectively, and the first increasing rate falling within a range between one-sixteenth and one of the second increasing rate.

More preferably, the first increasing rate is one-ninth of the second increasing rate.

The medical lancet may further include a holding region of biodegradable material connected to the second ascending region.

In one of the modifications of the present invention, the medical lancet further includes at least one channel extending in the predetermined direction through at least one of the first and second ascending regions and descending region.

Also, the holding region has at least one chamber in communication with the channel. The channel has at least one opening.

Preferably, the channel has at least two openings spaced away from each other by a predetermined gap.

More preferably, a plurality of the channels are provided, and the holding region has a plurality of the chambers, each of the chambers being in communication with corresponding one of the channels.

In another one of the modifications of the present invention, the medical lancet further includes at least one groove extending in the predetermined direction through at least one of the first and second ascending regions and descending region.

Also, in further modification, the medical lancet further includes a plurality of vertical cavities extending in a vertical direction perpendicular to the predetermined direction, and a seal membrane of biodegradable material for sealing the vertical cavities. The seal membrane has the thickness in the vertical direction varying based upon the position of each of the vertical cavities.

According to the second aspect of the present invention, a medical lancet includes a first ascending region, a descending region, and a second ascending region subsequently and integrally formed of biodegradable material. Those regions extend from a point in a predetermined direction, each of the regions having trapezoidal cross sections taken along any planes perpendicular to the predetermined direction. The first and second ascending regions have the trapezoidal cross sections of which base monotonically increases as being away from the point. The descending region has the trapezoidal cross sections of which base monotonically decreases as being away from the point. The first and second ascending regions have the largest cross section having substantially the same size and shape to each other.

Preferably, the medical lancet further includes at least one additional descending and ascending regions subsequently and integrally formed of biodegradable material and connected to the second ascending region, extending in the predetermined direction. Each of the additional descending and ascending regions has the trapezoidal cross sections taken along any planes perpendicular to the predetermined direction, of which base monotonically increases and decreases as being away from the point, respectively. The ascending regions have the largest cross section have substantially the same size and shape to each other.

Preferably, the smallest cross section in the descending region has the base greater than a half of the base of the largest cross section in the ascending regions.

More preferably, the smallest cross section in the descending region has the base greater than two-thirds of the base of the largest cross section in the ascending regions.

Further preferably, the largest cross sections in the first and second ascending regions are spaced away from each other by a gap greater than one micron.

Also, the medical lancet preferably further includes a constant region integrally formed of biodegradable material between the descending region and the second ascending region, having trapezoidal cross sections taken along any planes perpendicular to the predetermined direction, of which base is constant.

Preferably, the base of the trapezoidal cross sections in the first and second ascending regions are linearly increased at first and second increasing rates, respectively, and the first increasing rate falling within a range between one-fourth and one of the second increasing rate.

More preferably, the first increasing rate is one-third of the second increasing rate.

Further scope of applicability of the present invention will become apparent from the detailed description given hereinafter. However it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will more fully be understood from the detailed description given hereinafter and accompanying drawings which are given by way of illustration only, and thus are not limitative of the present invention.

FIGS. 4A-4C are front elevational, side, and top views of the medical lancet shown in FIG. 3, respectively.

FIGS. 9A-9C are front elevational, side, and top views of the medical lancet shown in FIG. 8, respectively.

FIGS. 11A-11C are side, top, and rear elevational views of the medical lancet of the first modification.

FIGS. 14A and 14B are side and bottom views of a medical lancet of the second modification.

FIGS. 15A and 15B are side views of another medical lancet of the second modification.

FIGS. 18A-18C are front elevational, side, and top views of the medical lancet shown in FIG. 15B, respectively.

DETAILED DESCRIPTION OF THE PREFERRED EMBODIMENTS

Referring to the attached drawings, the details of embodiments according to the present invention will be described hereinafter. In those descriptions, although the terminology indicating the directions (for example, "X-direction", "Y-direction", and "Z-direction") are conveniently used just for clear understandings, it should not be interpreted that those terminology limit the scope of the present invention.

Embodiment 1

Figure 1:
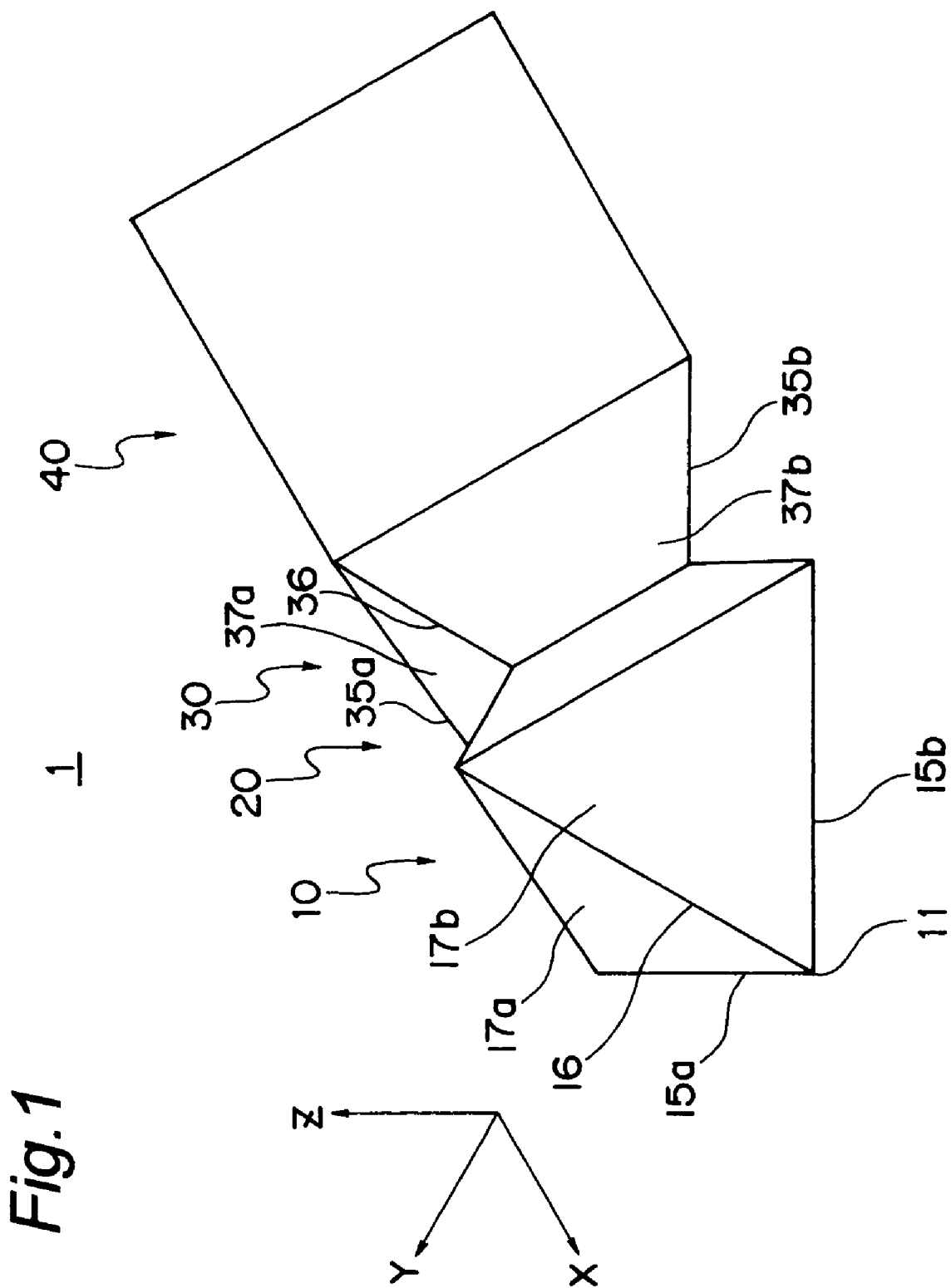
FIG. 1 is a perspective view of a medical lancet according to the first embodiment of the present invention.

With reference to FIGS. 1 to 4, the first embodiment of the medical lancet according to the present invention will be described herein. The medical lancet 1 is used to sample a drop of blood of a patient such as a diabetic for measurement of the blood sugar by stinging itself on the appropriate portion (e.g., fingertip) of the patient's body. As illustrated in FIGS. 1 and 2, the lancet 1 extends along the X-direction and has a triangle cross section as taken along any Y-Z planes. The triangle cross section includes base, height, and area varying in accordance with the distance from a lancet point 11 or the position of the X-axis. Thus, the lancet 1 includes a first ascending region (first tissue incising region) 10 of which area is monotonically increased as being away from the point 11, a first descending region (first friction releasing region) 20 of which area is monotonically decreased as being away from the point 11, and a second ascending region (second tissue incising region) 30. A holding region 40 is connected to the second ascending region 30 of the lancet 1.

According to the present invention, the lancet 1 is integrally formed of biodegradable material including for example, poly lactic acid, poly glycolic acid, poly caprolactone, collagen, amylum, hyaluronic acid, alginic acid, chitin, chitosan, cellulose, gelatin, and the compound/composition/copolymer/poly-microparticle thereof. Preferably, the holding region 40 is also integrally formed of the same material as that of the remaining regions. Therefore, the lancet 1 is degradable by micro-organisms so that once used it is easily deposited for landfill without raising any disposal problems unlike the metal lancet. Further, even if a portion of the lancet 1, for example when broken between the ascending and descending regions, is stuck within the patient body, the biodegradable material of the lancet 1 gives no harmful affect to the patient.

Next, referring to FIGS. 2A to 2C, the structure of the regions 10, 20, 30 composing the lancet 1 will be described in more detail. Each of the first and second ascending regions 10, 30 and the first descending region 20 has an outer configuration registered with the respective portion of a particular rectangle pyramid.

Figure 2A:
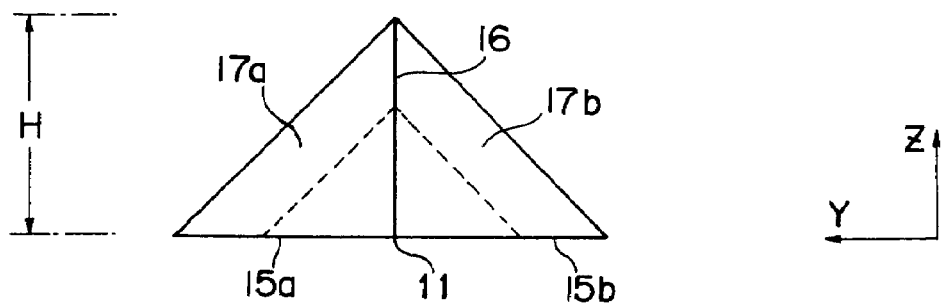
FIGS. 2A-2C are front elevational, side, and top views of the medical lancet shown in FIG. 1, respectively.
Figure 2B:
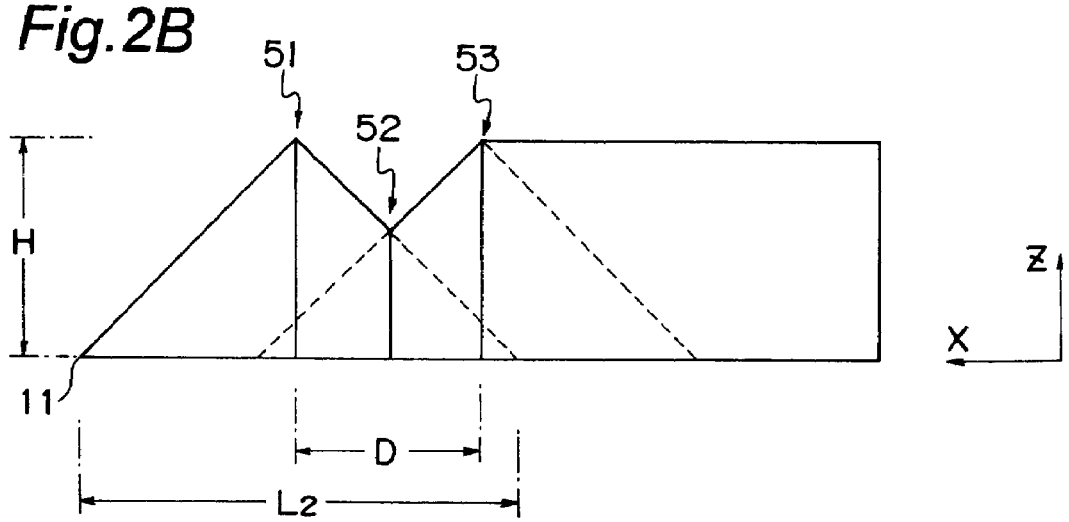
Figure 2C:
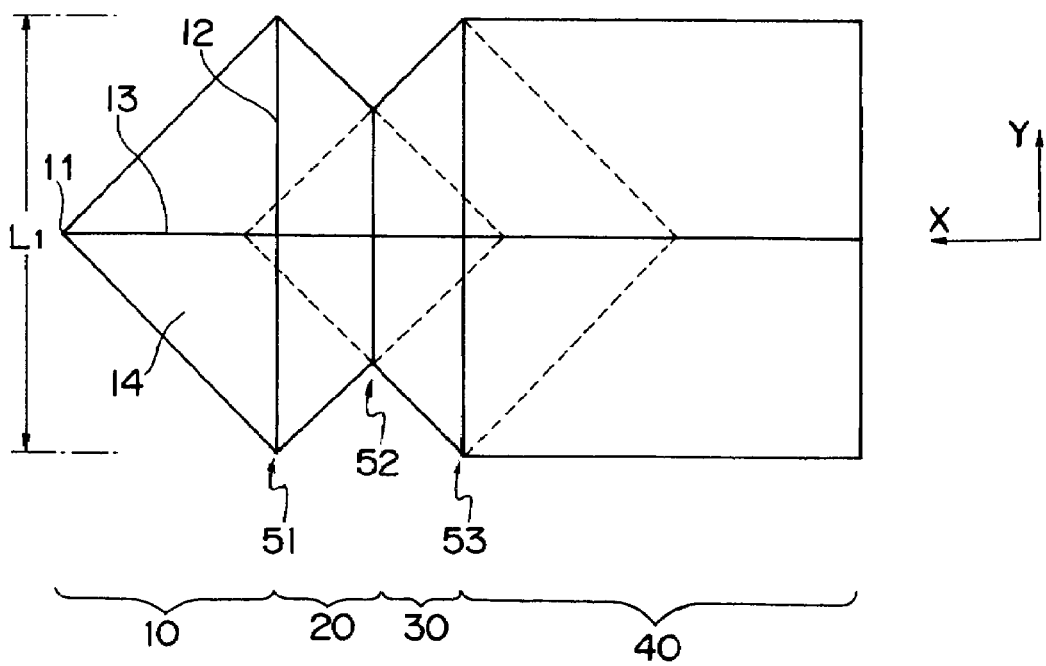

The rectangle pyramid has a predetermined height (H) as shown in FIGS. 2A and 2B, and a rhombic base 14 having first and second predetermined diagonals 12 ($L_1$), 13 ($L_2$), respectively. Preferably, the base is shaped as a square so that the first and second diagonals 12, 13 have the same length ($L_1=L_2$). Further, the height of the rectangle pyramid has a half of the length of the first and second diagonals 12, 13 ($H=L_1/2=L_2/2$), where the side surface (e.g., 17a, 17b) of the rectangle pyramid has a shape of an equilateral triangle.

In particular, the first ascending region 10 has an outer configuration registered with a first portion of the particular rectangle pyramid taken along the Y-Z plane 51 as shown in FIG. 2B. The first descending region 20 has an outer configuration registered with a second portion of the rectangle pyramid taken along and between the Y-Z planes 51 and 52. Also, the second ascending region 30 has an outer configuration registered with a third portion of the rectangle pyramid taken along and between the Y-Z planes 52 and 53. As above, those regions 10, 20, 30 of the lancet 1 are integrally formed such that each of the regions includes a base surface arranged on the same X-Y plane and the second diagonal arranged on the same line along the x-axis. It should be noted that each of the rectangle pyramid configuring the respective region has substantial the same dimension.

In the lancet 1 so structured, the cross sections taken along any Y-Z planes are triangle and include a base, a height, and an area lineally increasing or decreasing depending upon the distance from a lancet point 11 or the position of the X-axis. In the above description, the increase and decrease in size of the regions 10, 20, 30 are explained as being linear functions of the distance from the lancet point 11 or the position along the x-axis. However, it should be noted that the base, the height, and the area of the cross section in those regions may be defined as any non-linear functions such as a second or higher order functions which monotonically increases or decreases. Thus, the base, the height, and the area of the regions can be described by a linear or non-linear function monotonically increasing or decreasing as the parameter of the position along the x-axis.

According to the first embodiment of the present invention, the largest cross sections in the first and second ascending regions 10, 30 having the maximum area (i.e., the cross sections taken along the Y-Z planes 51 and 53) has triangular shapes, which are congruent with each other and similar to the smallest cross section in the first descending regions 20 having the minimum area (i.e., the cross section taken along the Y-Z plane 52).

Figure 3:
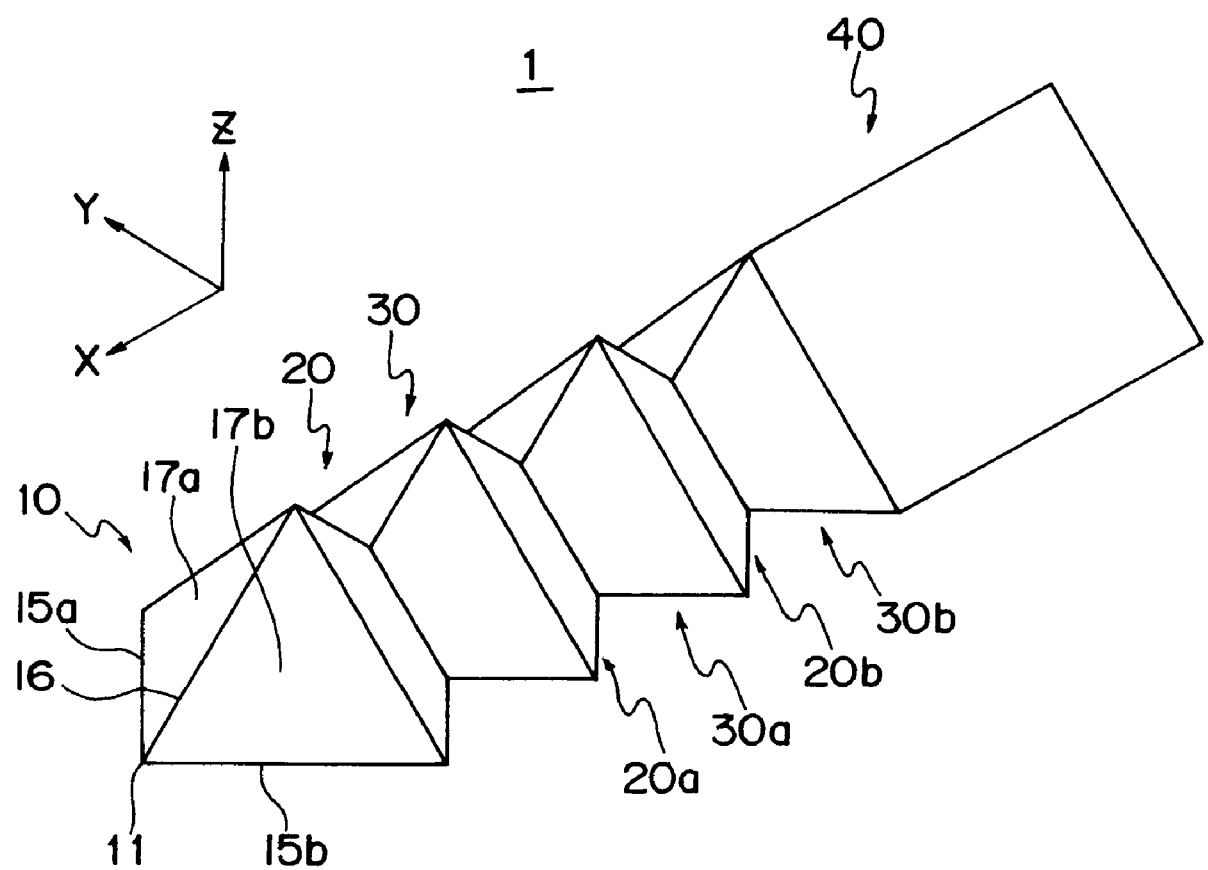
FIG. 3 is a perspective view of another medical lancet according to the first embodiment.

Preferably, the lancet 1 of the first embodiment includes at least one additional descending region 20a, 20b and the ascending region 30a, 30b as shown in FIGS. 3 and 4. In the additional ascending region 30a, 30b, the largest cross sections having the maximum area also have substantially the same shape and size as those of the other largest cross sections.

According to the lancet 1 illustrated in FIGS. 1 to 3, when being penetrated deeply inside the tissue (skin or flesh) of the patient's body, firstly, three of the members (sharp ridge lines) 15a, 15b, 15c of the rectangle pyramid incise the peripheral cells around the point 11 of the first ascending region (first tissue incising region) 10. Then, the bottom surface 14 and the side surfaces 17a, 17b of the first ascending region 10 wedge away the intact (non-incised) tissues into the deep inside. Thus, the first incising region 10 cuts and advances into the peripheral cells in a smooth manner. As the first incising region 10 advances into the tissue, the frictional force is increased between the surfaces 14, 17a, 17b of the first incising region 10 and the peripheral tissue, so that the peripheral tissue may be drawn into the deep inside by the increased frictional force.

However, after the first incising region 10 sinks within the tissue, and as the lancet 1 is further penetrated inside the tissue, the frictional force between the peripheral tissue and first descending region (first friction releasing region) 20 is released, since the first friction releasing region 20 has the cross section reducing or shrinking in size as being away from the point 11. Once the frictional force with the first incising region 10 is released, the peripheral tissue drawn inside by the frictional force will be reverted to the normal position by its elasticity. Thus, the peripheral tissue drawn by the first incising region 10 is returned to the original state so that the physical stress applied to the peripheral cells is reduced or minimized. Therefore, when the lancet 1 is penetrated into the tissue by the half length ($L_1/2$) of the second diagonal of the rectangle pyramid, the peripheral cells drawn inside are released from the frictional force to be replaced, thereby preventing the peripheral cells from being collapsed. This minimizes the pain-producing chemical mediator to give substantially less pain to the patient, and avoids the unrecoverable damage (collapse) of the peripheral cells across a substantial area around the point 11.

Again, after the first releasing region 20 sinks within the tissue, and as the lancet 1 further advances deeply inside the tissue, three of the members 35a, 35b, 35c of the second ascending region 30 incise substantially the same peripheral cells as the first ascending region cuts. Also, the bottom surface and the side surfaces 37a, 37b of the second ascending region 30 get the intact (non-incised) tissues out of the way, avoiding the unrecoverable damage of the peripheral cells. As above, since the largest cross sections of the first and second ascending regions 10, 30 are congruent with each other having substantially the same size and shape, the number of the incised cells can be minimized when the lancet 1 is penetrating inside the patient's body.

Thus, the penetrating process of the lancet 1 according to the present invention is achieved by repeatedly incising the peripheral cells and wedging away the intact tissues by the ascending regions 10, 30, and releasing the frictional force with the peripheral cells by the descending region 20 to replace thereof in its original position. Also, the present invention provides a non-invasive lancet 1 minimizing the pain to the patient by returning the peripheral cells across the substantial area back to the original position and by avoiding the damage of the peripheral cells.

Meanwhile, although depending upon the portion of patient's body, one of the peripheral cells has a size of about 10 microns in general, and in particular, the microcyte in the micro-vessel has the size of 5 microns. The rectangle pyramid is designed so as to have the first and second diagonals ($L_1$, $L_2$) and the height (H) of about 85 to 180 microns and about 42.5 to 90 microns, respectively. Thus, the largest cross section in the ascending regions 10, 30 has a triangle shape having a base of about 85 to 180 microns and a height of about 42.5 to 90 microns.

When the base and the height of the smallest cross section taken along the Y-Z plane 52 are approximately less than a half of those of the largest cross section taken along the Y-Z planes 51, 53, the medical lancet 1 has insufficient strength so that it tends to break off between the descending region 20 and the second ascending region 30. Thus, if the base and the height of the smallest cross section are approximately less than about 42.5 to 90 microns and about 21.2 to 45 microns, respectively, then the lancet 1 is easily broken off. Therefore, the lancet 1 of the embodiment is designed such that the base and the height of the smallest cross section are approximately greater than a half of those of the largest cross section, and thus the smallest cross section is approximately greater than a quarter (square of a half) of the largest cross section. More preferably, the lancet 1 is designed such that the base and the height of the smallest cross section is approximately greater than two-thirds (⅔) of those of the largest cross section, and thus the smallest cross section is approximately greater than four-ninths (4/9: square of ⅔) of the largest cross section. This realizes a stubborn and reliable lancet 1 without breaking off and/or bending so as to secure piercing into the patient's body.

Also, the descending region 20 should have the size for releasing the frictional stress of the peripheral cells, i.e., the size of at least one cell, thus as illustrated in FIG. 2A, the gap (D) between the adjacent largest cross sections taken along the Y-Z planes 51 and 53 is designed to have at least one (1) micron and preferably five (5) microns.

Figure 5A:
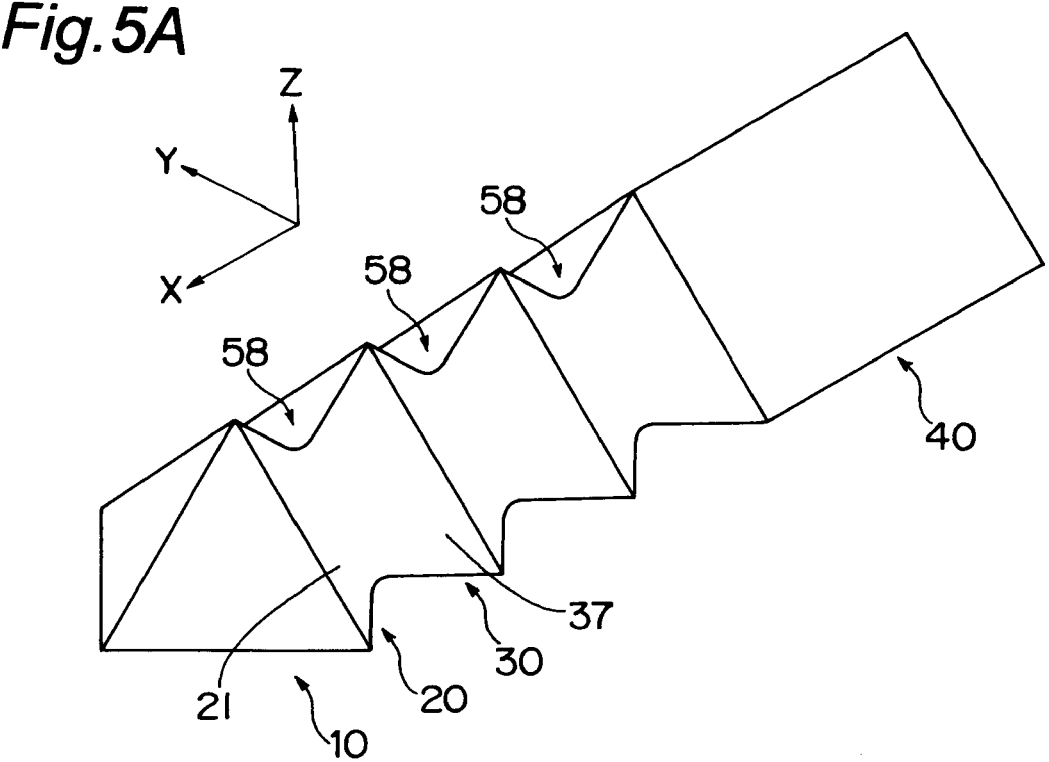
FIGS. 5A-5C are perspective, side, and top views of another medical lancet according to the first embodiment.
Figure 5B:
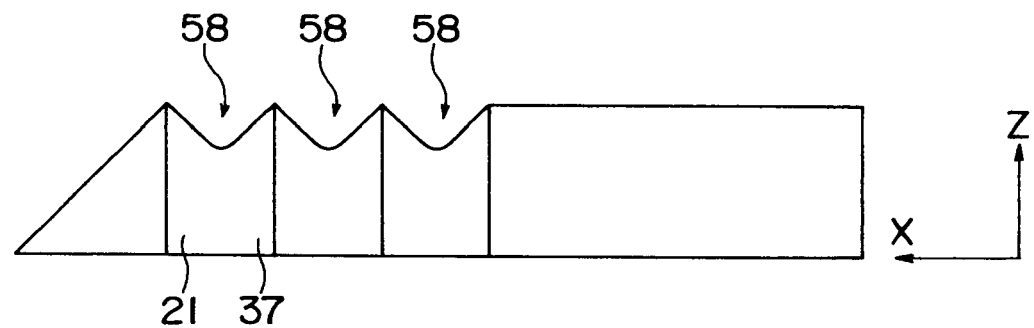
Figure 5C:
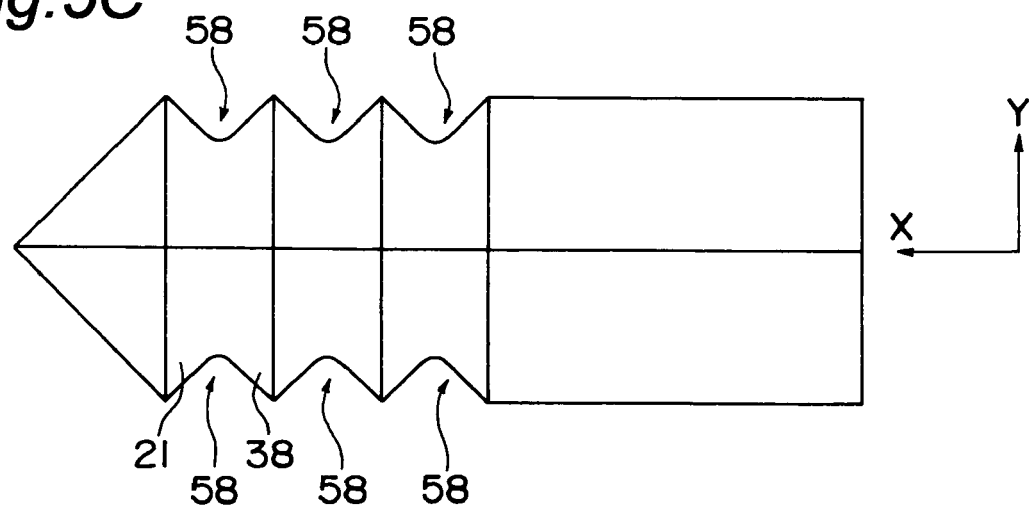

As above, the side surfaces 21, 37 of the descending region 20 and second ascending region 30 are described as flat planes so that an angled portion (discontinuous portion) is formed therebetween. Contrary, as illustrated in FIG. 5, the lancet 1 may have a continuous curved portion 58 smoothly connecting the side surfaces 21, 37 of the descending region 20 and second ascending region 30. The continuous curved portion 58 makes the lancet 1 even stiffer against the stress otherwise concentrated on that portion.

Also, it should be noted that although the cross section of the holding region 40 taken along any Y-Z planes is illustrated to be a triangle, it can be a rectangle or any other shapes for appropriate fit to an external holder mechanism (not shown).

Embodiment 2

With reference to FIGS. 6 to 9, the second embodiment of the medical lancet according to the present invention will be described herein. The medical lancet 2 of the second embodiment is similar to the medical lancet 1 of the first embodiment except that it additionally includes a constant region (reinforcing region). Therefore, the duplicated description in detail for the common features will be eliminated.

Figure 6:
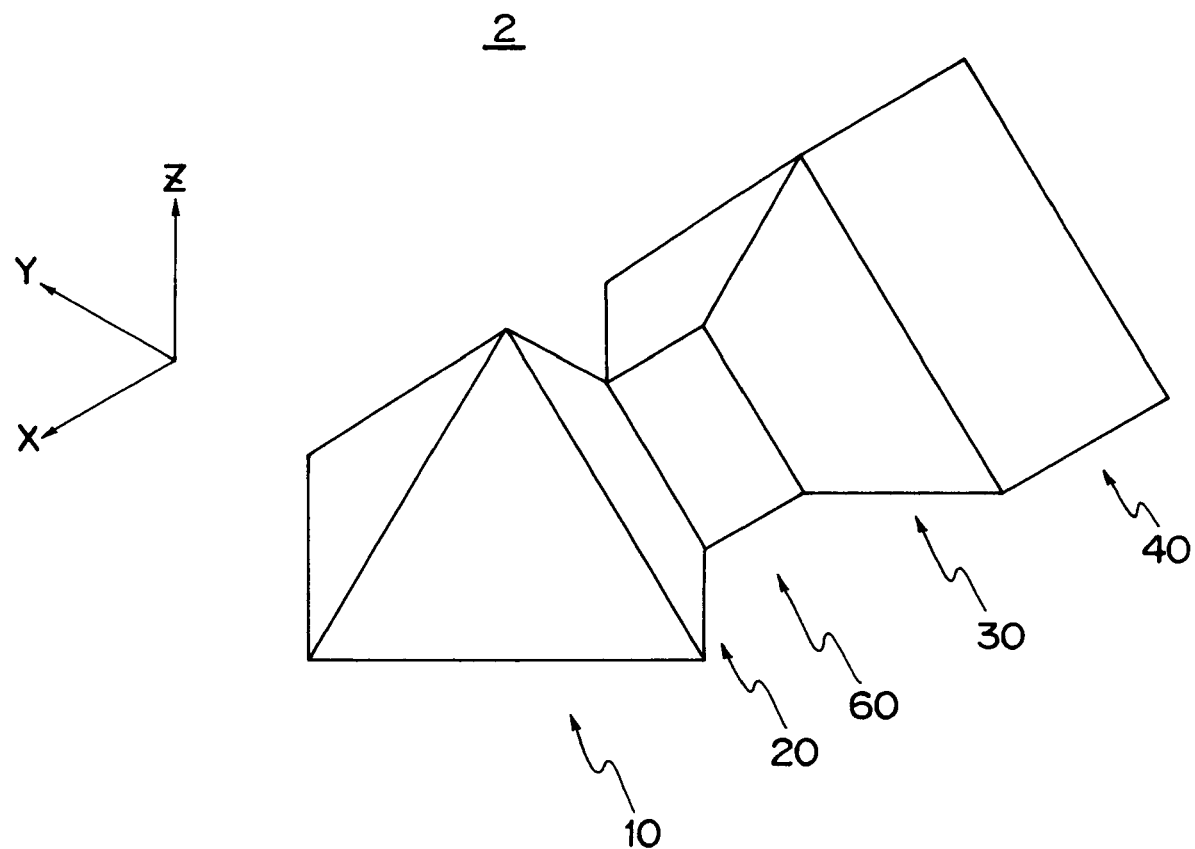
FIG. 6 is a perspective view of a medical lancet according to the second embodiment of the present invention.
Figure 7A:
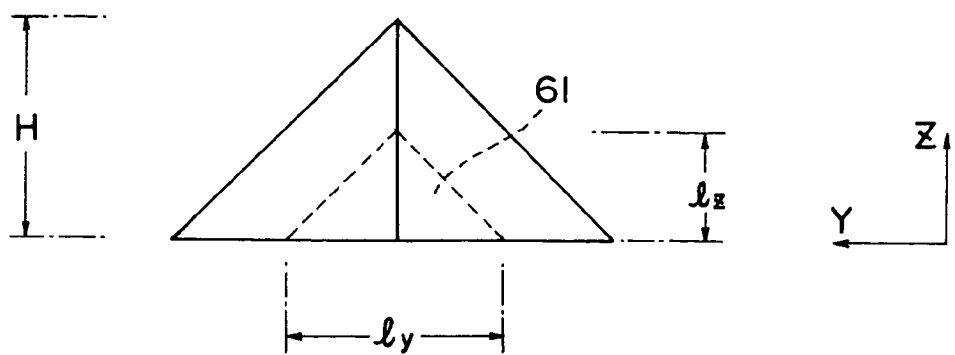
FIGS. 7A-7C are front elevational, side, and top views of the medical lancet shown in FIG. 6, respectively.
Figure 7B:
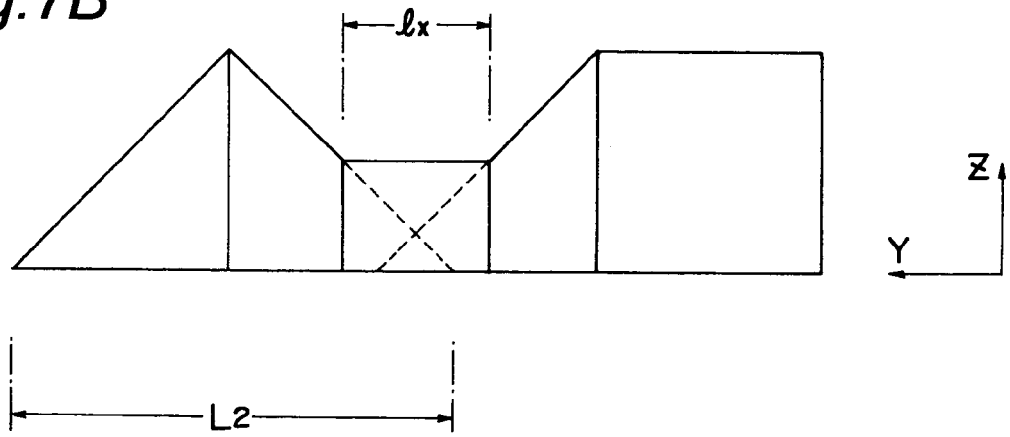
Figure 7C:
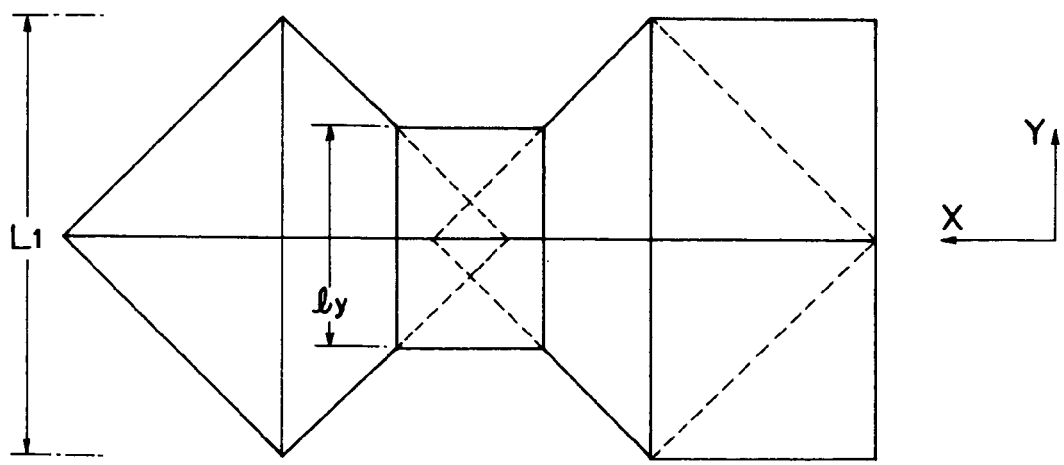

As above, the medical lancet 2 of the second embodiment has a constant region (reinforcing region) 60 for reinforcing the strength of the lancet 2 between the first descending region 20 and the second ascending region 30 as shown in FIGS. 6 and 7. The constant region 60 has an outer configuration of a triangular prism having a size of X-, Y-, and Z-directions ($l_x$, $l_y$, $l_z$) with a triangular base 61 that is substantially the same shape and size as the smallest cross section in the descending region 20. Thus, the constant region 60 has a triangle cross section having a base ($l_y$) and a height ($l_z$) as taken along any Y-Z planes.

According to the second embodiment, similar to the first embodiment, the base and the height ($l_y$, $l_z$) of the constant region 60 are designed to be approximately greater than a half, preferably a two-thirds (⅔) of those of the largest cross section ($L_1$, H), respectively, i.e., $$l_y \geq L_1/2,\ l_z \geq H/2;\text{ and preferably,}$$

$$l_y \geq 2L_1/3,\ l_z \geq 2H/3.$$

This design reinforces the strength between the descending region. 20 and the second ascending region 30 so as to realize a more stubborn lancet 2.

Figure 8:
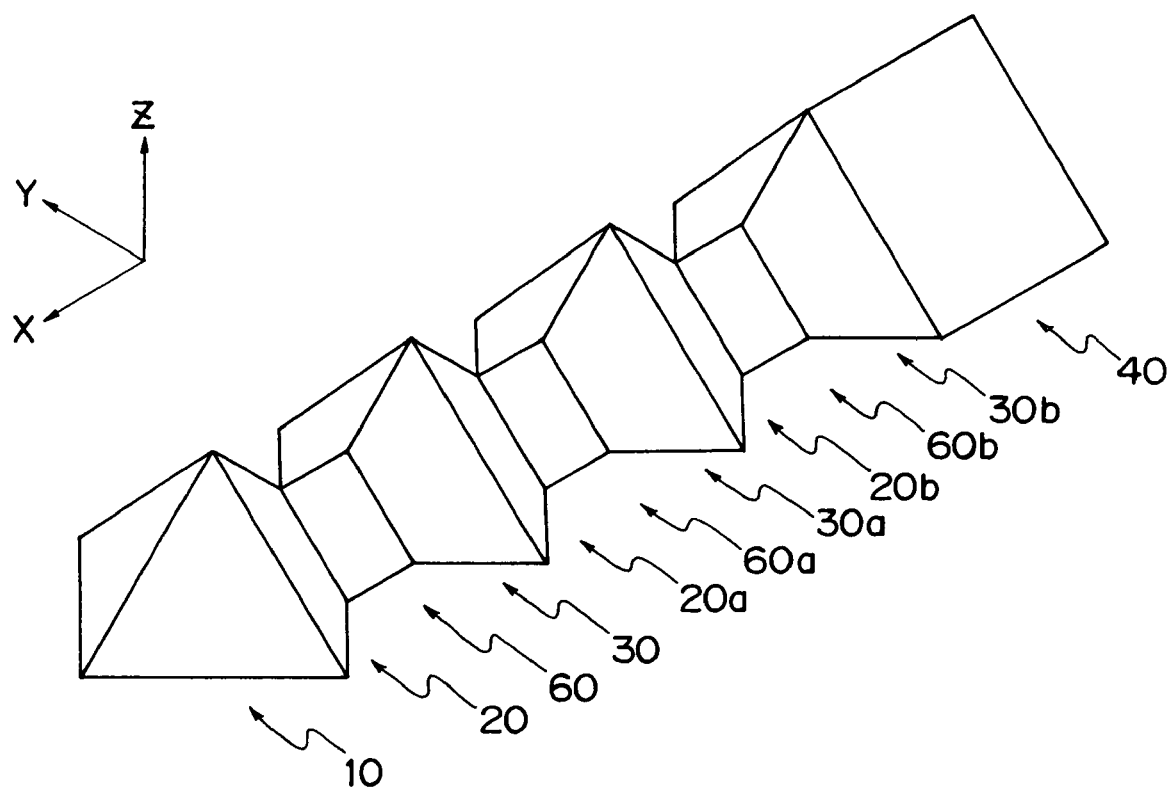
FIG. 8 is a perspective view of another medical lancet according to the second embodiment.

Also as the first embodiment, the lancet 2 of the second embodiment may include at least one additional descending region 20a, 20b, the constant region 60a, 60b, and the ascending region 30a, 30b, as illustrated in FIGS. 8 and 9.

Embodiment 3

With reference to FIG. 10, the third embodiment of the medical lancet according to the present invention will be described herein. The medical lancet 3 of the third embodiment is similar to the medical lancet 1 of the first embodiment except that the lancet point is formed sharper than that of the first embodiment. Therefore, the duplicated description in detail for the common features will be eliminated.

Figure 10A:
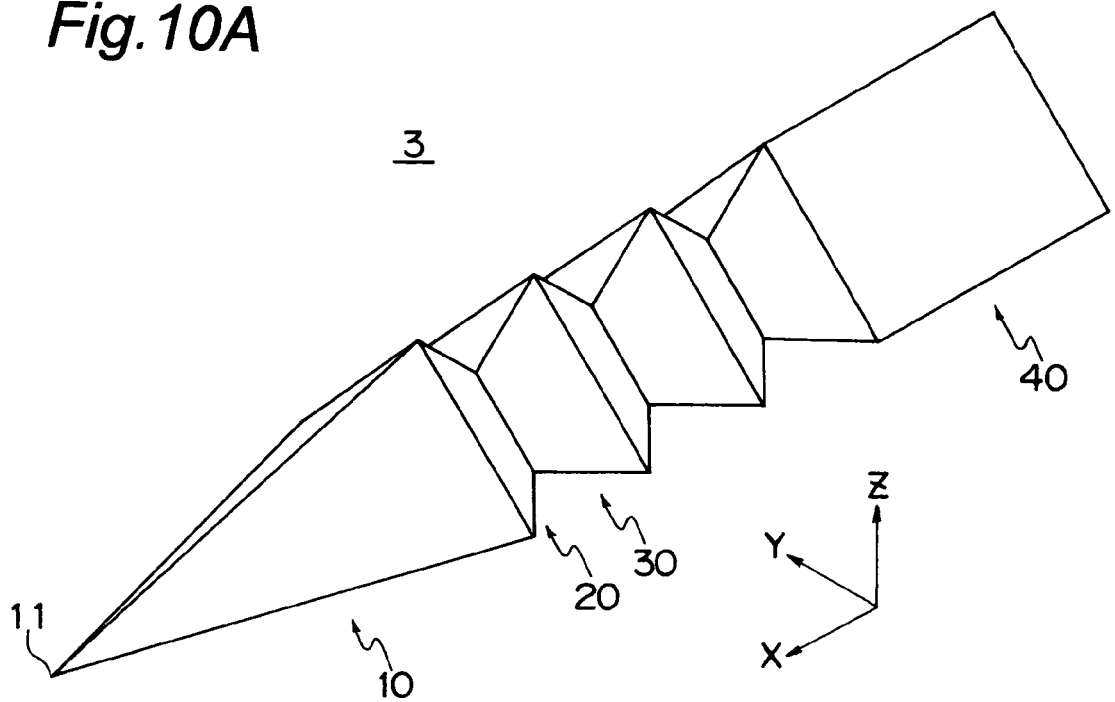
FIGS. 10A-10C are perspective, side, and top views of a medical lancet according to the third embodiment of the present invention.
Figure 10B:
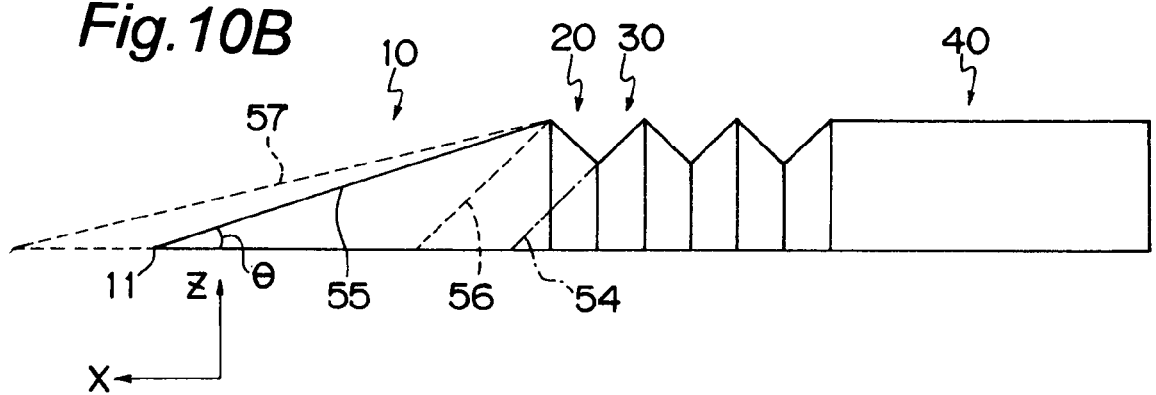
Figure 10C:
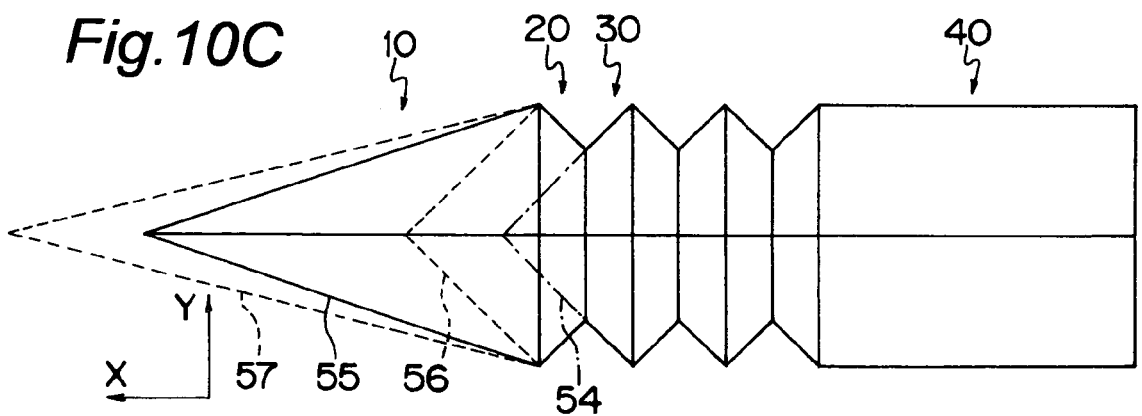

In FIGS. 10B and 10C, the first and second ascending region 10, 30 are designed so as to have the triangular cross section taken along any Y-Z planes, of which height and base are increased linearly as being away from the point 11 with gradients (increasing rates) indicated by a solid line 55 and a one-dotted line 54, respectively. Also, the increasing rate (k) of the height and base of the first ascending region 10 indicated by the solid line 55 varies from an increasing rate ($k_1$) indicated by one imaginary line 56 to another increasing rate ($k_2$) indicated by another imaginary line 57, i.e., $k_2(57) \leq k(55) \leq k_1(56)$.

The imaginary line 56 is parallel to the one-dotted line 54 of the second ascending region 30 having the increasing rate ($k_0$), and the other imaginary line 57 is approximately a quarter of the increasing rate ($k_0$), i.e., $k_0/4(57) \leq k(55) \leq k_0(56)$.

Preferably, the increasing rate (k) of the height and the base of the first ascending region 10 is set to one-third (⅓) of the increasing rate ($k_0$) of the second ascending region 30, i.e., $k = k_0/3$.

Therefore, when the increasing rate of the cross section (area) of the second ascending region 30 is represented by ($K_0$), the increasing rate (K) of the cross section (area) of the first ascending region 10 falls within a range between one-sixteenth (¹⁄₁₆; square of a quarter) and one of the second ascending region 30, i.e., $K_0/16 \leq K \leq K_0$.

Preferably, the increasing rate (K) of the cross section of the first ascending region 10 is set to one-ninth (⅑; square of ⅓) of the increasing rate ($K_0$) of the second ascending region 30, i.e., $K = K_0/9$.

For example, suppose if the rectangle pyramid defining the outer configuration of the ascending and descending regions includes the first and second diagonals ($L_1$, $L_2$) of the same length and the height that is the same as a half of the diagonals, i.e., $H = L_1/2 = L_2/2$. Then, the first ascending region has the length in the X-direction varying between $L_1/2$ to $2L_1$, preferably $3L_1/2$, and also the point angle (θ) indicated in FIG. 10B varies between about 14 degree to 45 degrees, preferably is about 18.3 degree.

According to the lancet 3 of the third embodiment, height and the base of the cross section in the first ascending region 10 are more moderately increased than those in the second ascending region 30 so that lancet point 11 of the embodiment is sharper and more elongated. This contributes the lancet 3 of the third embodiment to be penetrated more smoothly into the deep inside with less resistance, thereby further reducing the pain to the patient.

As persons skilled in the art can easily conceives, the medical lancet of foregoing embodiments can be manufactured, for example, by use of ROMONANO α-0iAR commercially available from a FUNAC Ltd. in Yamanashi Pref., JAPAN.

(Modification 1)

Figure 12A:
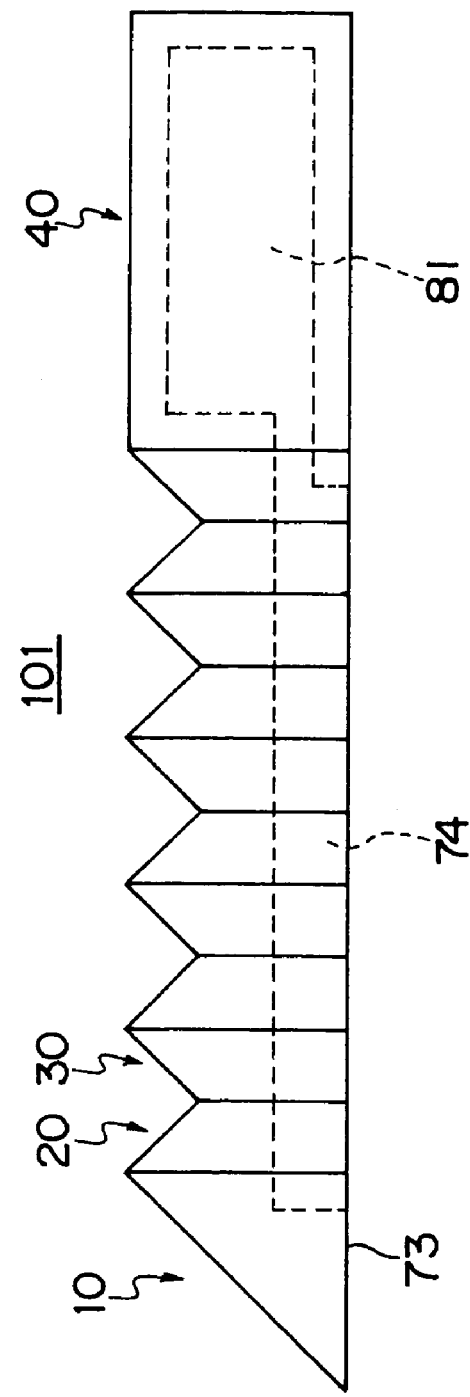
FIGS. 12A and 12B are side and bottom views of another medical lancet of the first modification.
Figure 12B:
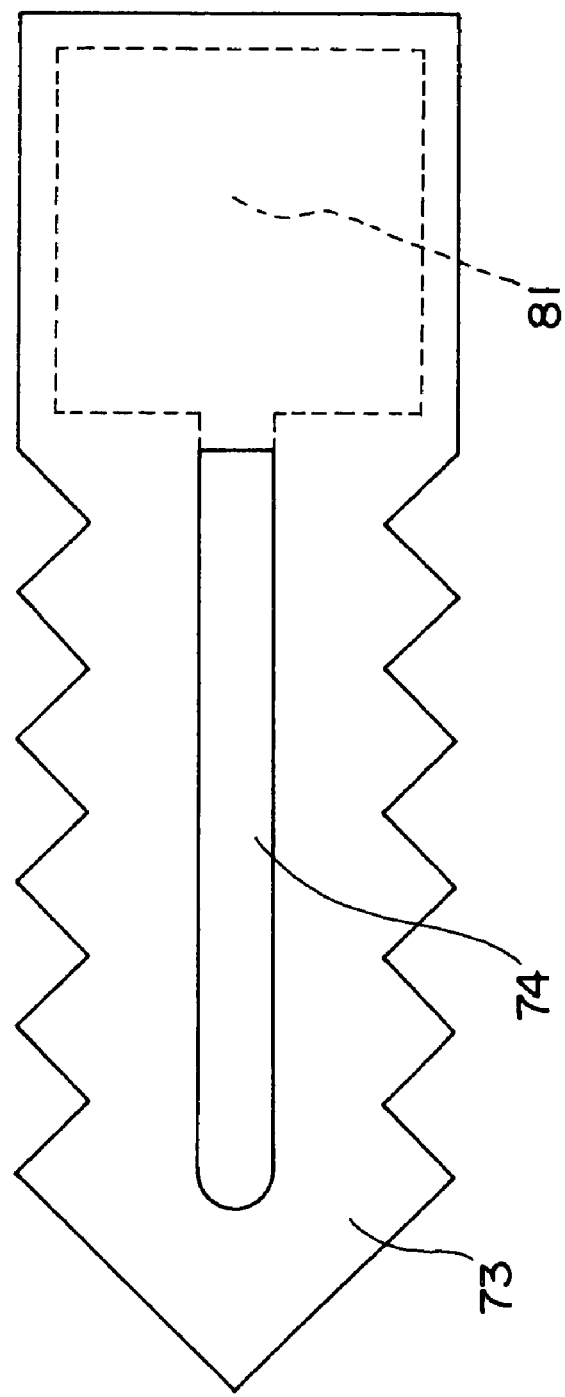

With reference to FIGS. 11 to 13, the first modification of the medical lancet will be described herein. The medical lancet 101 of the first modification is similar to the medical lancets 1, 2, 3 of the first to third embodiments except that at least one channel and chamber are provided within the lancet. Therefore, the duplicated description in detail for the common features will be eliminated.

The lancet 101 of the first modification includes at least one channel 71 extending through the incising regions 10, 30 and the releasing region 20 of the lancet 101 as illustrated in FIG. 11A. Preferably, the holding region 40 includes at least one chamber 81 in communication with the channel 71, which has the rectangular cross section taken along any Y-Z planes as shown in FIG. 11C. Also, the lancet 101 has at least one opening 72 close to the point 11, extending through any appropriate surfaces such as the bottom surface 73 of the descending region 20.

The lancet 101 having the channel 71 and the chamber 81 can be used in various applications. For example, a pair of electrodes (not shown) spaced away from each other may be arranged within the channel 71 and also a bio-sensor (not shown) such as a Micro Total Analysis System (µ-TAS) may be received in the chamber 81.

When the lancet 101 so structured is penetrated into the body, the channel 71 and the opening 72 have such a small diameter performing as a capillary tube that the blood plasma in a fluid form is drawn through the opening 72 into the channel 71, thereby to contact with the electrodes. Thus, a sufficient amount of the blood plasma is filled within the channel 71 to be analyzed without using a complicated pump mechanism for aspirating the blood plasma into the channel 71. It is well known that the amount of fluid drawn in the capillary tube is in inverse proportion to the diameter of the channel 71 and the opening 72. Therefore, the diameters of the channel 71 and the opening 72 can appropriately be selected to control the amount of the aspirated blood plasma. Also, the diameter of the opening 72 is preferably 10 microns or less to prevent the red and white blood cells from entering the channel 71.

As above, according to the lancet 101 so constructed, immediately after stinging the lancet 101 onto the patient's body, it can draw the sufficient and controlled amount of the blood plasma through the opening 72 into the channel 71, and readily analyze the component of the blood plasma, without using the complicated mechanism.

Instead of the channel 71 and the opening 72 as shown in FIG. 11, the lancet 101 may include a groove 74 extending along the X-direction on the bottom surface 73 as illustrated in FIG. 12. Also, the lancet 101 may include a pair of electrodes arranged within the channel 71 and also a bio-sensor received in the chamber 81 to analyze the desired component of the blood. When the lancet of FIG. 12 is pierced inside the patient's body, the groove 74 in cooperation with the peripheral tissue also defines the capillary tube so that the blood plasma is filled sufficiently within the groove 74.

Figure 13A:
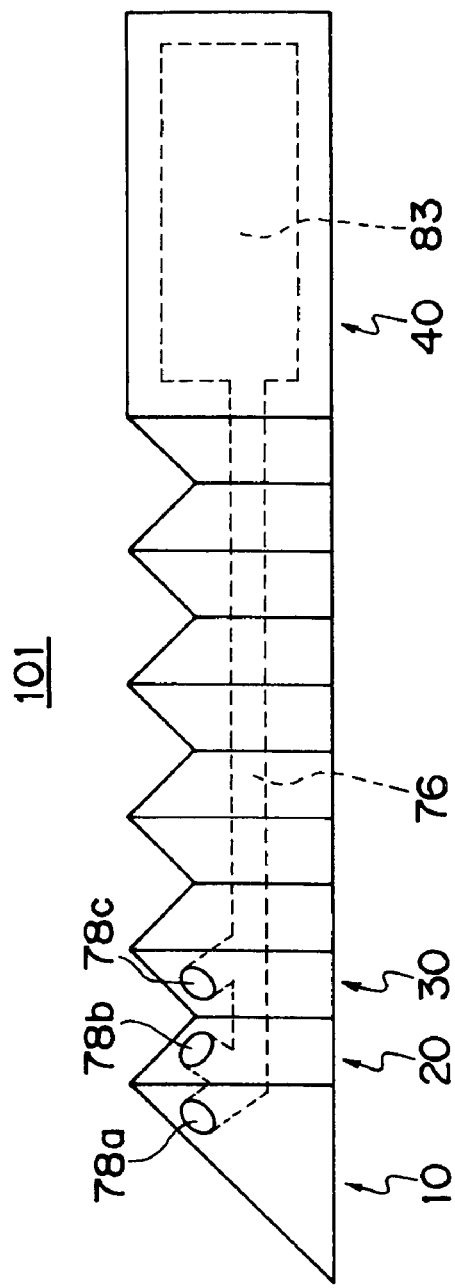
FIGS. 13A and 13B are side and top views of further another medical lancet of the first modification.
Figure 13B:
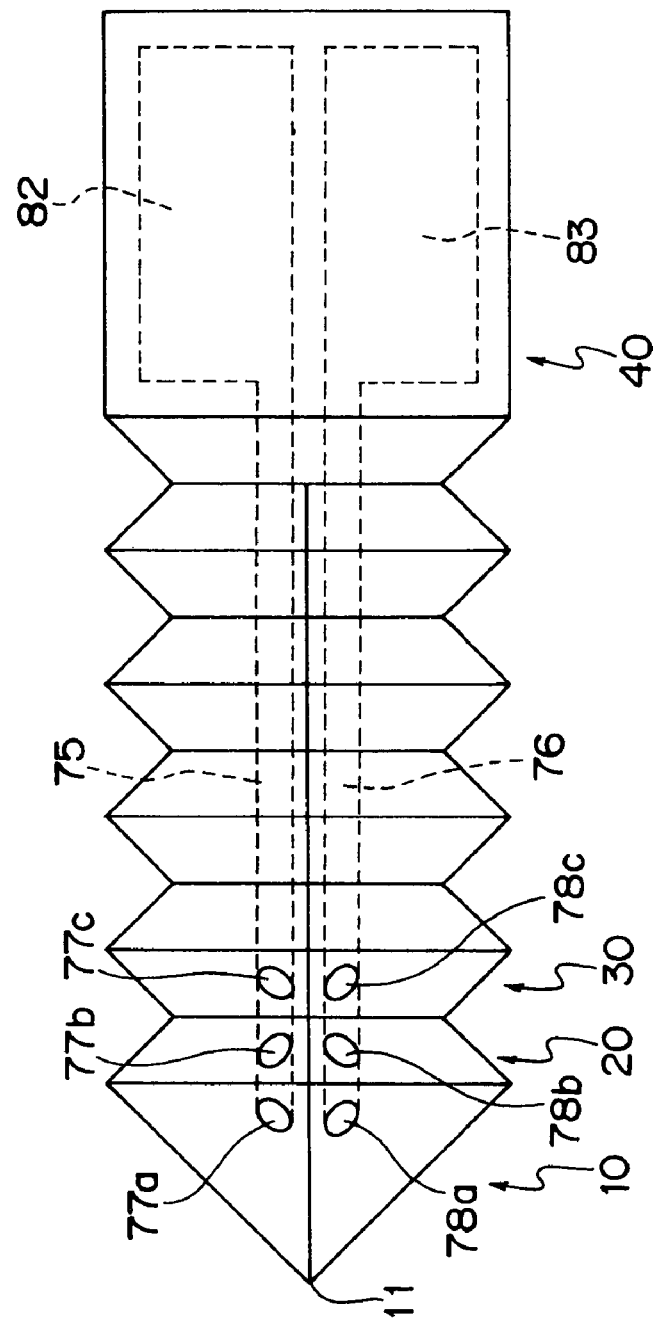

Alternatively, the lancet 101 of the modification may include a plurality of channels extending in the X-direction and a plurality of chambers in the holding region 40, each separately communicating with corresponding one of the chambers (two channels 75, 76 and two chambers 82, 83 are shown in FIG. 13). Also, a plurality of openings 77a-77c, and 78a-78c are formed adjacent the point 11, for example, extending through the side surfaces of the regions 10, 20, 30 as illustrated in FIGS. 13A and 13B. Each of the channels 75, 76 may receive the independent electrode pairs and also each of the chambers 82, 83 may include a different bio-sensors therein for analyzing a plurality types of blood components.

It should be noted that the channels 75, 76 and openings 77a-77c, and 78a-78c of the lancet 101 shown in FIG. 13 also define capillary tubes, and the., diameters thereof are selected appropriately in accordance with the desired amount of the aspirated blood plasma.

Further, plural kinds of medicaments may be reserved within the chambers 82, 83 for gradually releasing the medicaments into the patient's body through the openings 77, 78. If desired, each of the openings 77, 78 may be sealed by a sheet (not shown) made of biodegradable material same as that of the lancet 101 so as to allow the medicaments to be gradually released a predetermined time after the lancet 101 is stuck in the tissue of the patient. In addition, the thickness of the sheets may be changed depending upon the channels 75, 76 so that the timing for gradual release of the medicaments can be controlled.

More preferably, the adjacent openings 77, 78 are spaced away from each other by a predetermined gap. One example is where each of the electrodes is assembled to be extruded through the respective one of openings 77, 78, then the distance between the electrodes is defined exactly, allowing the fluid between the electrodes to be analyzed in a more precise manner. Also, another example is where a pair of fiber optics are extruded through the openings 77b and 77c so that beams from each of the fiber optics intersect each other, then the fluid at the intersection of the beam can be inspected more accurately due to the precisely defined geometry.

(Modification 2)

With reference to FIGS. 14 and 15, the second modification of the medical lancet will be described herein. The medical lancet 102 of the second modification is similar to the medical lancets 1, 2, 3 of the first to third embodiments except that a vertical cavity and a seal membrane for sealing the vertical cavity are provided within the lancet. Therefore, the duplicated description in detail for the common features will be eliminated.

As above, the medical lancet 102 of the second modification includes at least one vertical cavity (four vertical cavities 91a-91d are shown in FIGS. 14A, 14B) extending in a vertical direction (Z-direction) and a seal membrane 92 for sealing the vertical cavity. The vertical cavity 91 receives a micro-particle or fluid containing medicament therein. Also, the seal membrane 92 is made of biodegradable material so that in conjunction with the lancet 102, it seals the vertical cavity to secure the medicament therein without slipping off from the vertical cavity 91.

When the lancet 102 is penetrated and held permanently within the patient body, especially, the biodegradable material especially composing the seal membrane 92 is gently degraded so that medicament contained within the micro-particle or the like received in the vertical cavity 91 is gradually released. Preferably, in case where a plurality of cavities for different medicaments are provided, the seal membrane 92 is designed such that it has the thickness in the Z-direction varying based upon the position of the vertical cavities 91a-91d. In one example shown in FIG. 15A, the seal membrane 92 has the thickness tapered towards the point 11, and in another example shown in FIG. 15B, the seal membrane 92 is stepped such that it is the thinnest at the cavity 91a, and the second thinnest at the cavity 91b, and the thickest at the last cavity 91d. This structure controls the timing for gradual release of the medicament received in the vertical cavities 91a-91d.

It should be noted that as persons skilled in the art easily conceive and practice, the channel 71, the chamber 81, the openings 77, 78, and the vertical cavities 91a-91d of the first and second modifications are formed with use of a laser device such as an excimer laser emitting laser beam having adjustable power.

Embodiment 4

With reference to FIGS. 16 to 18, the fourth embodiment of the medical lancet will be described herein. The medical lancet 4 of the fourth embodiment is similar to the medical lancet 1 of the first embodiment except that while the latter has the triangular cross sections taken along any Y-Z planes, the former has the trapezoidal cross sections taken along any Y-Z planes. Therefore, the duplicated description in detail for the common features will be eliminated.

Figure 16A:
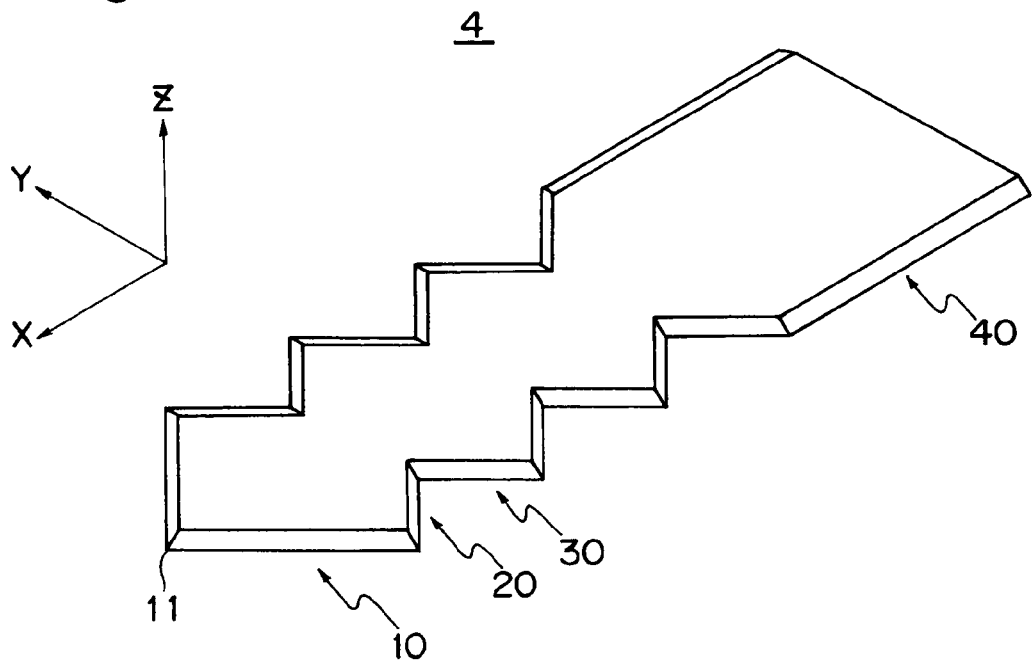
FIGS. 16A and 16B are perspective views of a medical lancet according to the fourth embodiment of the present invention.
Figure 16B:
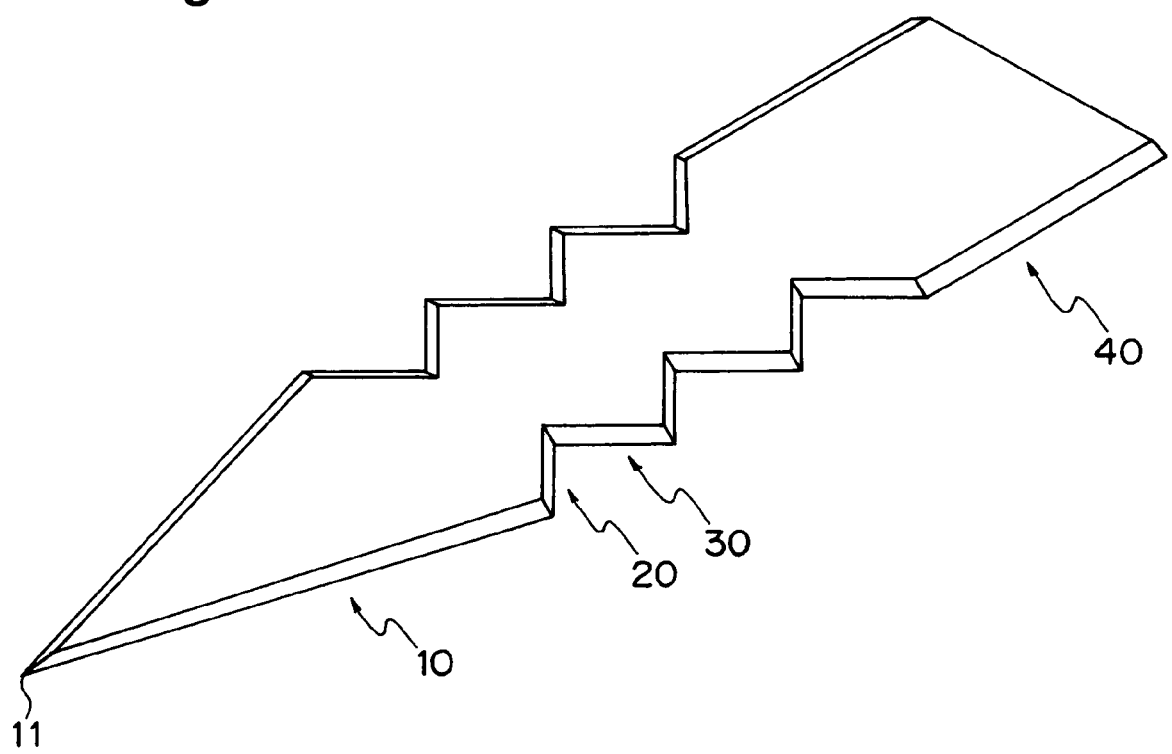
Figure 17A:
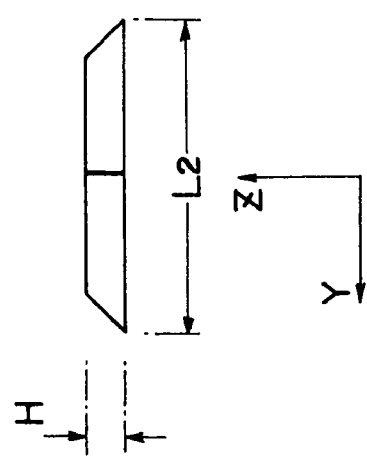
FIG. 17A-17C are front elevational, side, and top views of the medical lancet shown in FIG. 15A, respectively.
Figure 17B:
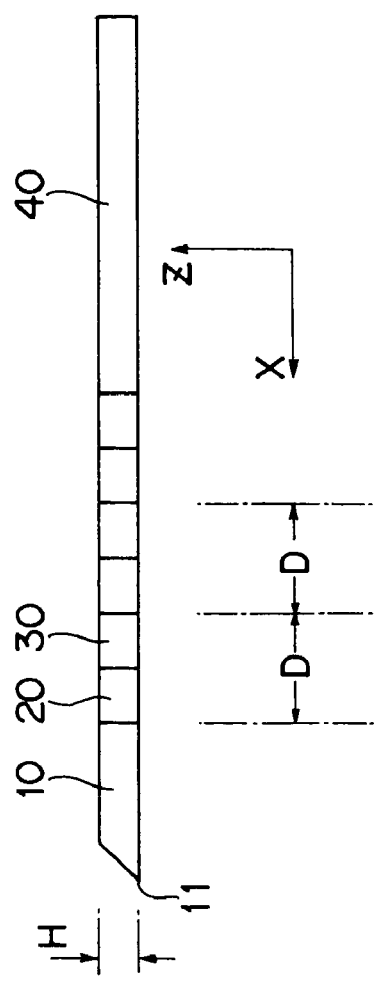
Figure 17C:
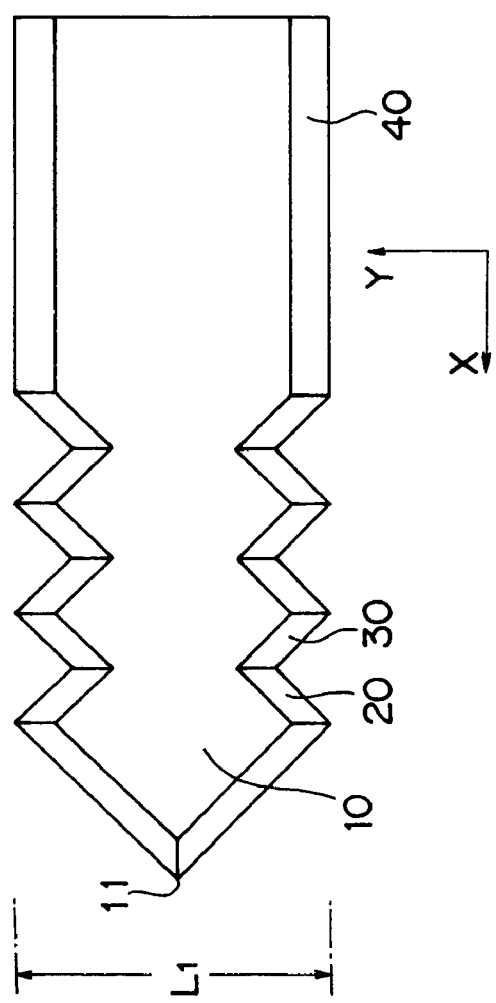

As clearly understood by comparing FIGS. 3 and 10A of the first embodiment with FIGS. 16A and 16B of the fourth embodiment, respectively, and by referring FIGS. 17A and 17B, the lancet 4 of the present embodiment has the trapezoidal, rather than triangular, cross sections taken along any Y-Z planes. The trapezoid has the base (i.e., each of the upper and lower bases) varying in accordance with the distance from the lancet point 11 or the position in the X-direction, and the height (H) that is constant. Thus, the lancet 4 of the present embodiment includes first and second ascending regions (first and second tissue incising regions) 10, 30, of which trapezoidal cross sections taken along any Y-Z planes has the base monotonically increasing as being away from the point 11, a first descending region (first friction releasing region) 20 of which trapezoidal cross sections taken along any Y-Z planes has the base monotonically decreasing as being away from the point 11. Also, the holding region 40 is connected with the subsequent ascending region 20. Since the lancet of the present invention is integrally made of the aforementioned biodegradable material, it can be disposed without any environment problems, and also be retained in the patient's body.

According to the fourth embodiment, the first and second ascending regions 10, 30 have the largest trapezoidal cross section, of which bases have substantially the length same as each other. Also, although in view of incising the peripheral cells or tissue, the height (H) of the trapezoidal cross section is preferably short (the lancet 4 is thin), however, the height has to be taller than a predetermined dimension for ensuring sufficient strength of the lancet 4. In particular, the lancet 4 of the embodiment preferably has the thickness (H) greater than about one-eighth of the base of the largest cross section, i.e., the first diagonal ($L_1$) of the rectangular pyramid (i.e., $H \leq L_1/8$).

In FIGS. 17A-17C and 18A-18C; the base of the smallest cross section is preferably greater than a half, and more preferably greater than about two-thirds of the largest cross section. Also, like the first embodiment, the largest cross sections in first and second ascending regions 10, 30 adjacent to each other is spaced away preferably by a predetermined gap (D) of at least 1 micron.

Further, similar to the first embodiment, the lancet 4 of the fourth embodiment may include at least one additional descending region and ascending region integrally formed with the second ascending region 20. Also, similar to the second embodiment, the lancet 4 of the fourth embodiment may include at least one additional constant (reinforcing) region having the cross section of substantially the constant area, which is formed between the descending and ascending regions.

In addition, similar to the third embodiment, the first ascending region 10 of the lancet 4 is designed sharper such that the base of the trapezoidal cross section increases gently. The increasing rate of the base of the trapezoidal cross section in the first ascending region 10 falls within a range between about one-fourth and one of the increasing rate of the trapezoidal cross section in the second ascending region 30. Thus, the lancet 4 of the fourth embodiment is sharp so that it can easily be penetrated into the tissue, minimizing the pain to the patient.

What is claimed is:

1. A medical lancet, comprising:
   a first ascending region having a sharp point, a descending region, and a second ascending region subsequently and integrally formed of biodegradable material, extending from the point in a predetermined direction, each of said regions having triangular cross sections taken along any planes perpendicular to the predetermined direction;
   said first and second ascending regions having the triangular cross sections of which area monotonically increases as being away from the point; and
   said descending region having the triangular cross sections of which area monotonically decreases as being away from the point;
   wherein said first and second ascending regions have the largest cross section having substantially the same size and shape to each other.

2. A medical lancet according to claim 1, further comprising:
   at least one additional descending and ascending regions subsequently and integrally formed of biodegradable material and connected to said second ascending region, extending in the predetermined direction;
   wherein each of said additional descending and ascending regions has the triangular cross sections taken along any planes perpendicular to the predetermined direction, of which area monotonically decreases and increases as being away from the point, respectively; and
   wherein said first and second ascending regions have the largest cross section having substantially the same size and shape to each other.

3. The medical lancet according to claim 1,
   wherein the smallest cross section in the descending region is similar to the largest cross section in the ascending regions, and
   wherein the smallest cross section in the descending region has an area greater than one-fourth of the area of the largest cross section in the ascending regions.

4. The medical lancet according to claim 3,
   wherein the smallest cross section in the descending region has an area greater than four-ninths of the area of the largest cross section in the ascending regions.

5. The medical lancet according to claim 1,
   wherein the largest cross sections in said first and second ascending regions are spaced away from each other by a gap greater than one micron.

6. The medical lancet according to claim 1,
   wherein a continuous curved portion is provided between said descending region and said second ascending region for smoothly connecting thereof.

7. The medical lancet according to claim 1, further comprising:
   a constant region integrally formed of biodegradable material between said descending region and said second ascending region, having triangular cross sections taken along any planes perpendicular to the predetermined direction, of which area is constant.

8. The medical lancet according to claim 1,
   wherein the area of the triangular cross sections in the first and second ascending regions are linearly increased at first and second increasing rates, respectively, and the first increasing rate falling within a range between one-sixteenth and one of the second increasing rate.

9. The medical lancet according to claim 8,
   wherein the first increasing rate is one-ninth of the second increasing rate.

10. The medical lancet according to claim 1, further comprising:
    a holding region of biodegradable material connected to said second ascending region.

11. The medical lancet according to claim 1, further comprising:
    at least one channel extending in the predetermined direction through at least one of said first and second ascending regions and descending region.

12. The medical lancet according to claim 11,
    wherein said holding region has at least one chamber in communication with said channel.

13. The medical lancet according to claim 12,
    wherein said channel has at least one opening.

14. The medical lancet according to claim 11,
    wherein said channel has at least two openings spaced away from each other by a predetermined gap.

15. The medical lancet according to claim 11,
    wherein said at least one channel includes a plurality of channels, and
    wherein said holding region has a plurality of chambers, each of the chambers being in communication with corresponding one of said plurality of channels.

16. The medical lancet according to claim 1, further comprising:
    at least one groove extending in the predetermined direction through at least one of said first and second ascending regions and descending region.

17. The medical lancet according to claim 1, further comprising:
    a plurality of vertical cavities extending in a vertical direction perpendicular to the predetermined direction; and
    a seal membrane of biodegradable material for sealing said vertical cavities;
    wherein the seal membrane has the thickness in the vertical direction that varies based upon the position of each of the vertical cavities.

18. A medical lancet, comprising:
    a first ascending region having a sharp point, a descending region, and a second ascending region subsequently and integrally formed of biodegradable material, extending from the point in a predetermined direction, each of said regions having trapezoidal cross sections taken along any planes perpendicular to the predetermined direction;
    said first and second ascending regions having the trapezoidal cross sections of which base monotonically Increases as being away from the point; and
    said descending region having the trapezoidal cross sections of which base monotonically decreases as being away from the point;
    wherein said first and second ascending regions have the largest cross section having substantially the same size and shape to each other.

19. The medical lancet according to claim 18, further comprising:

at least one additional descending and ascending regions subsequently and integrally formed of biodegradable material and connected to said second ascending region, extending in the predetermined direction;

wherein each of said additional descending and ascending regions has the trapezoidal cross sections taken along any planes perpendicular to the predetermined direction, of which base monotonically decreases and increases as being away from the point, respectively; and wherein said first and second ascending regions have the largest cross section having substantially the same size and shape to each other.

20. The medical lancet according to claim 18, wherein the smallest cross section in the descending region has a base greater than a half of the base of the largest cross section in the ascending regions.

21. The medical lancet according to claim 20, wherein the smallest cross section in the descending region has a base greater than two-thirds of the base of the largest cross section in the ascending regions.

22. The medical lancet according to claim 18, wherein the largest cross sections in said first and second ascending regions are spaced away from each other by a gap greater than one micron.

23. The medical lancet according to claim 18, further comprising:

a constant region integrally formed of biodegradable material between said descending region and said second ascending region, having trapezoidal cross sections taken along any planes perpendicular to the predetermined direction, of which base is constant.

24. The medical lancet according to claim 18, wherein the base of the trapezoidal cross sections in the first and second ascending regions are linearly increased at first and second increasing rates, respectively, and the first increasing rate falling within a range between one-fourth and one of the second increasing rate.

25. The medical lancet according to claim 24, wherein the first increasing rate is one-third of the second increasing rate.

26. The medical lancet according to claim 18, further comprising:

a holding region of biodegradable material connected to said second ascending region.

* * * * *